US010160959B2

(12) United States Patent
Goins et al.

(10) Patent No.: US 10,160,959 B2
(45) Date of Patent: *Dec. 25, 2018

(54) TRPV1 MODULATORY GENE PRODUCT THAT AFFECTS TRPV1-SPECIFIC PAIN BEHAVIORAL RESPONSES IDENTIFIED IN A FUNCTIONAL SCREEN OF AN HSV-BASED CDNA LIBRARY

(71) Applicant: University of Pittsburgh—Of the Commonwealth System of Higher Education, Pittsburgh, PA (US)

(72) Inventors: William F. Goins, Pittsburgh, PA (US); Joseph C. Glorioso, III, Pittsburgh, PA (US); Justus Bernard Cohen, Pittsburgh, PA (US); Bonnie L. Reinhart, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,521

(22) Filed: Feb. 24, 2017

(65) Prior Publication Data
US 2017/0283782 A1 Oct. 5, 2017

Related U.S. Application Data

(63) Continuation of application No. 14/690,038, filed on Apr. 17, 2015, now Pat. No. 9,580,699.

(60) Provisional application No. 61/980,925, filed on Apr. 17, 2014.

(51) Int. Cl.
*C12N 9/16* (2006.01)
*A61K 38/46* (2006.01)
*A61K 48/00* (2006.01)
*C07K 14/47* (2006.01)
*A61K 9/00* (2006.01)
*A61K 47/02* (2006.01)
*A61K 9/08* (2006.01)

(52) U.S. Cl.
CPC .............. *C12N 9/16* (2013.01); *A61K 38/46* (2013.01); *A61K 48/005* (2013.01); *C07K 14/4703* (2013.01); *A61K 9/0019* (2013.01); *A61K 9/0085* (2013.01); *A61K 9/08* (2013.01); *A61K 47/02* (2013.01); *C12N 2710/16643* (2013.01); *C12N 2799/028* (2013.01); *C12N 2830/008* (2013.01)

(58) Field of Classification Search
CPC ........... A61K 38/46; A61K 48/00; C12N 9/16
USPC .................................................... 435/320.1
See application file for complete search history.

(56) References Cited

U.S. PATENT DOCUMENTS

| | | | |
|---|---|---|---|
| 5,658,724 A | 8/1997 | DeLuca | |
| 5,804,413 A | 9/1998 | DeLuca | |
| 5,849,571 A | 12/1998 | Glorioso et al. | |
| 5,849,572 A | 12/1998 | Glorioso et al. | |
| 5,879,934 A | 3/1999 | DeLuca | |
| 5,998,174 A | 12/1999 | Glorioso et al. | |
| 6,261,552 B1 | 7/2001 | DeLuca | |
| 7,078,029 B2 | 7/2006 | DeLuca | |
| 7,531,167 B2 | 5/2009 | Glorioso et al. | |
| 7,825,231 B2 | 11/2010 | Wolfe et al. | |
| 8,003,622 B2 | 8/2011 | Wolfe et al. | |
| 8,309,349 B2 | 11/2012 | Glorioso et al. | |
| 9,580,699 B2 * | 2/2017 | Goins | A61K 48/005 |
| 2002/0090382 A1 | 7/2002 | Glorioso | |
| 2002/0090719 A1 | 7/2002 | Yew | |
| 2005/0202559 A1 | 9/2005 | Pownall et al. | |
| 2007/0178069 A1 | 8/2007 | Glorioso et al. | |
| 2007/0207124 A1 | 9/2007 | Glorioso et al. | |
| 2008/0289058 A1 | 11/2008 | Cascio et al. | |
| 2009/0238807 A1 | 9/2009 | Glorioso et al. | |
| 2011/0213017 A1 | 9/2011 | Cascio et al. | |

FOREIGN PATENT DOCUMENTS

| | | |
|---|---|---|
| WO | WO 99/06583 A1 | 2/1999 |
| WO | WO 99/61067 A1 | 12/1999 |
| WO | WO 2006/050211 A2 | 5/2006 |
| WO | WO 2008/143875 A1 | 11/2008 |
| WO | WO 2011/130749 A2 | 10/2011 |

OTHER PUBLICATIONS

Akopian et al., "Transient receptor potential TRPA1 channel desensitization in sensory neurons is agonist dependent and regulated by TRPV1-directed internalization," *J. Physiol.*, 583(1): 175-193 (2007).
Amaya et al., "NGF and GDNF differentially regulate TRPV1 expression that contributes to development of inflammatory thermal hyperalgesia," *European Journal of Neuroscience*, 20: 2303-2310 (2004).
Barabas et al., "TRPA1 Is Functionally Expressed Primarily by IB4-Binding, Non-Peptidergic Mouse and Rat Sensory Neurons," *PLOS One*, 7(10): 1-12 (Oct. 2012).
Bohlen et al., "Receptor-targeting mechanisms of pain-causing toxins: How ow?" *Toxicon*, 60(3): 254-264 (2012).
Brederson et al., "Targeting TRP channels for pain relief," *European Journal of Pharmacology*, 716(1-3): 61-76 (2013).

(Continued)

*Primary Examiner* — Antonio Galisteo Gonzalez
(74) *Attorney, Agent, or Firm* — Leydig, Voit & Mayer, Ltd.

(57) ABSTRACT

The invention provides a method for ameliorating chronic pain signaling involving transient receptor potential cation channel subfamily V member 1 (TRPV1) by expressing PP1α in neurons. The invention also provides HSV vectors for expressing PP1α within neurons and compositions comprising such vectors.

15 Claims, 10 Drawing Sheets

(56) References Cited

OTHER PUBLICATIONS

Figure 1:
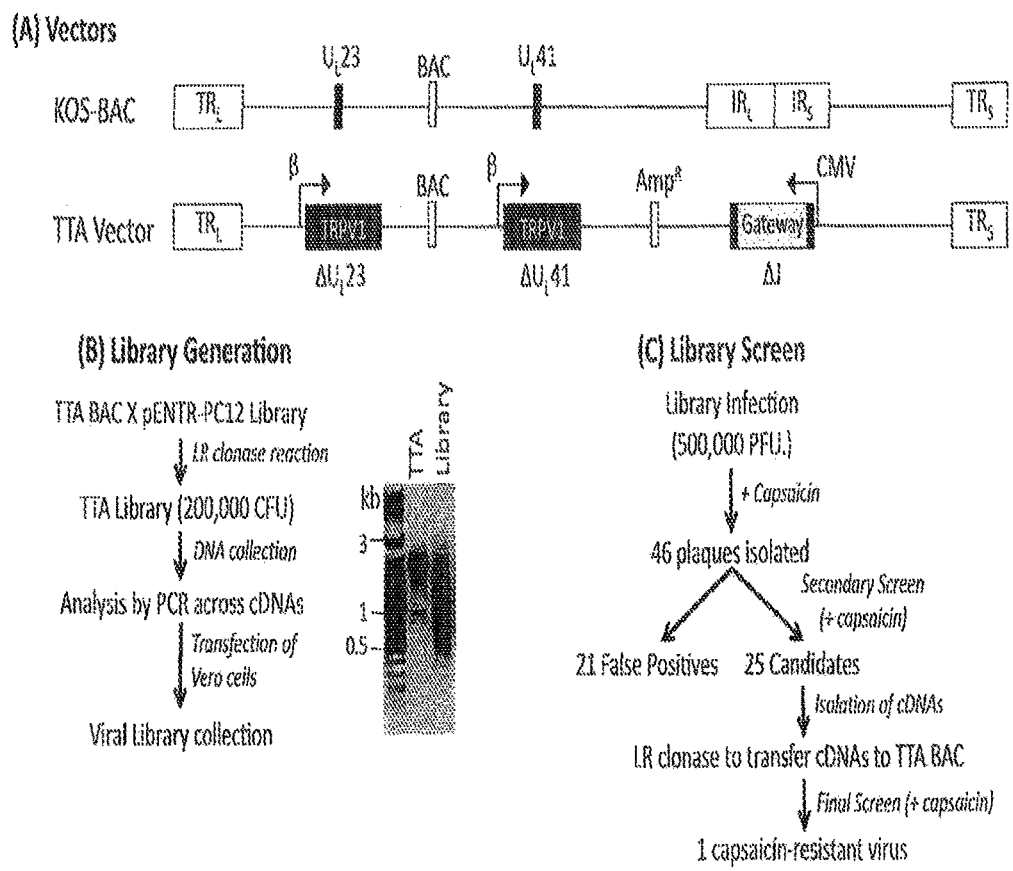

Caterina et al., "The capsaicin receptor: a heat-activated ion channel in the pain pathway," *Nature*, 389(6653): 816-824 (Oct. 23, 1997).
Caterina et al., "The Vanilloid Receptor: A Molecular Gateway to the Pain Pathway," *Annu. Rev. Neurosci.* 24: 487-517 (2001).
Chaudhury et al., "AKAP150-mediated TRPV1 sensitization is disrupted by calcium/calmodulin," *Molecular Pain*, 7(34): 1-13 (2011).
Chuang et al., "Bradykinin and nerve growth factor release the capsaicin receptor from PtdIns(4,5)$P_2$-mediated inhibition," *Nature*, 411: 957-962 (Jun. 21, 2001).
Dhaka et al., "TRP Ion Channels and Temperature Sensation," *Annu. Rev. Neurosci.*, 29: 135-161 (2006).
Docherty et al., "Inhibition of calcineurin inhibits the desensitization of capsaicin-evoked currents in cultured dorsal root ganglion neurones from adult rats," *Eur. J. Physiol.*, 431: 828-837 (1996).
Dubuisson et al., "The Formalin Test: A Quantitative Study of the Analgesic Effects of Morphine, Meperidine, and Brain Stem Stimulation in Rats and Cats," *Pain*, 4: 161-174 (1977).
Fink et al., "Gene Therapy for Pain: Results of a Phase I Clinical Trial," *Ann. Neurol.*, 70(2): 207-212 (2011).
Fischer et al., "The interphase of the formalin test," *Pain*, 155: 511-521 (2014).
Garcia-Sanz et al., "Identification of a Tetramerization Domain in the C Terminus of the Vanilloid Receptor," *The Journal of Neuroscience*, 24(23): 5307-5314 (Jun. 9, 2004).
Garry et al., "Varicella zoster virus induces neuropathic changes in rat dorsal root ganglia and behavioral reflex sensitization that is attenuated by gabapentin or sodium channel blocking drugs," *Pain*, 118(1-2): 97-111 (2005).
Gentry et al., "The roles of iPLA2, TRPM8 and TRPA1 in chemically induced cold hypersensitivity," *Molecular Pain*, 6(4): 1-11 (2010).
Gierasch et al., "Construction and characterization of bacterial artificial chromosomes containing HSV-1 strains 17 and KOS," *Journal of Virological Methods*, 135: 197-206 (2006).
Goss et al., "Antinociceptive effect of a genomic herpes simplex virus-based vector expressing human proenkephalin in rat dorsal root ganglion," *Gene Therapy* 8(7): 551-556 (2001).
Goss et al., "Herpes Vector-Mediated Expression of Proenkephalin Reduces Bone Cancer Pain," *Annals of Neurology*, 52(5): 662-665 (Nov. 2002).
Goss et al., "HSV Delivery of a Ligand-regulated Endogenous Ion Channel Gene to Sensory Neurons Results in Pain Control Following Channel Activation," *Molecular Therapy*, 19(3): 500-506 (Mar. 2011).
Hao et al., "HSV-mediated expression of interleukin-4 in dorsal root ganglion neurons reduces neuropathic pain," *Molecular Pain*, 2(6): 1-9 (Feb. 17, 2006).
Hao et al., "Effects of transgene-mediated endomorphin-2 in inflammatory pain," *European Journal of Pain*, 13(4): 380-386 (2009).
Hargreaves et al., "A new and sensitive method for measuring thermal nociception in cutaneous hyperalgesia," *Pain*, 32: 77-88 (1988).
Hucho et al., "Ca++/CaMKII switches nociceptor-sensitizing stimuli into desensitizing stimuli," *Journal of Neurochemistry*, 123(4): 589-601 (2012).
Jeske et al., "Cannabinoid WIN 55,212-2 Regulates TRPV1 Phosphorylation in Sensory Neurons," *The Journal of Biological Chemistry*, 281(43): 32879-32890 (Oct. 27, 2006).
Johannes et al., The Prevalence of Chronic Pain in United States Adults: Results of an Internet-Based Survey, *The Journal of Pain*, 11(11): 1230-1239 (Nov. 2010).
Kinchington et al., "Varicella zoster virus-induced pain and post-herpetic neuralgia in the human host and in rodent animal models," *J. Neurovirol.*, 17(6): 590-599 (2011).
Krisky et al., "Deletion of multiple immediate-early genes from herpes simplex virus reduces cytotoxicity and permits long-term gene expression in neurons," *Gene Therapy*, 5: 1593-1603 (1998).

Laing et al., "ThermoTRPs and Pain," *The Neuroscientist*, 1-17 (2015).
Lee et al., "Activation of NMDA receptors leads to phosphorylation of TRPV1 S800 by protein kinase C and A-Kinase anchoring protein 150 in rat trigeminal ganglia," *Biochemical and Biophysical Research Communication*, 424(2): 358-363 (2012).
MacDonald et al., "Genome Sequence of Herpes Simplex Virus 1 Strains KOS," *Journal of Virology*, 86(11): 6371-6372 (Jun. 2012).
MacPherson et al., "An Ion Channel Essential for Sensing Chemical Damage," *The Journal of Neuroscience*, 27(42): 11412-11415 (Oct. 17, 2007).
Majima et al., "Herpes Simplex Virus (HSV) Vector-Mediated Gene Delivery of Protein Phosphatase 1α Reduces Bladder Overactivity and Nociception in Rats," *The Journal of Urology*, 191(4S): Abstract MP1-03 (May 16, 2014).
Mandadi et al., "Increased sensitivity of desensitized TRPV1 by PMA occurs through PKCε-mediated phosphorylation at S800," *Pain*, 123(1-2): 106-116 (Jul. 2006).
Marconi et al., "Replication-defective herpes simplex virus vectors for gene transfer in vivo," *Proc. Natl. Acad. Sci. USA*, 93(21): 11319-11320 (Oct. 1996).
McNamara et al., "TRPA1 mediates formalin-induced pain," *Proc. Natl. Acad. Sci. USA*, 104(33): 13525-13530 (Aug. 14, 2007).
Miyazato et al., "Herpes simplex virus vector-mediated gene delivery of glutamic acid decarboxylase reduces detrusor overactivity in spinal cord-injured rats," *Gene Therapy*, 16(5): 660-668 (2009).
Miyazato et al., "Suppression of Detrusor-Sphincter Dyssynergia by Herpes Simplex Virus Vector Mediated Gene Delivery of Glutamic Acid Decarboxylase in Spinal Cord Injured Rats," *The Journal of Urology*, 184(3): 1204-1210 (Sep. 2010).
Mohapatra et al, "Regulation of $Ca^{2+}$-dependent Desensitization in the Vanilloid Receptor TRPV1 by Calcineurin and cAMP-dependent Protein Kinase," *The Journal of Biological Chemistry*, 280(14): 13424-13432 (Apr. 8, 2005).
Por et al., "PP2B/calcineurin-mediated desensitization of TRPV1 does not require AKAP150," *Biochem. J.*, 432(3): 549-556 (2010).
Premkumar et al., "Downregulation of Transient Receptor Potential Melastatin 8 by Protein Kinase C-Mediated Dephosphorylation," *The Journal of Neuroscience*, 25(49): 11322-11329 (Dec. 7, 2005).
Price et al., "Treatment of trigeminal ganglion neurons in vitro with NGF, GDNF or BDNF: effects on neuronal survival, neurochemical properties and TRPV1-mediated neuropeptide secretion," *BMC Neuroscience*, 6(4): 1-15 (Jan. 24, 2005).
Price et al., "Pharmacological interactions between calcium/calmodulin-dependent kinase II α and TRPV1 receptors in rat trigeminal sensory neurons," *Neuroscience Letters*, 389: 94-98 (2005).
Reinhart et al., "An HSV Based Selection Method for Isolation of Negative Regulators of TRPV1," *Molecular Therapy*, 19(Supplement 1): Abstract 53 S21 (May 2011).
Reinhart et al., "Identification of a Negative Regulator of TRPV1 Via an HSV Based cDNA Library Screen," *Molecular Therapy*, 21(Supplement 1): Abstract 478 S184 (May 2013).
Roberson et al., "Targeting of sodium channel blockers into nociceptors to produce long-duration analgesia: a systematic study and review," *British Journal of Pharmacology*, 164(1): 48-58 (2011).
Salas et al., "TRPA1-mediated responses in trigeminal sensory neurons: interaction between TRPA1 and TRPV1," *European Journal of Neuroscience*, 29(8): 1568-1578 (2009).
Sharma et al., "Mechanisms and clinical uses of capsaicin," *European Journal of Pharmacology*, 720: 55-62 (2013).
Srinivasan et al., "An HSV vector system for selection of ligand-gated ion channel modulators," *Nature Methods*, 4(9): 733-739 (Sep. 2007).
Srinivasan et al., "Protein kinase C epsilon contributes to basal and sensitizing responses of TRPV1 to capsaicin in rat dorsal root ganglion neurons," *European Journal of Neuroscience*, 28(7): 1241-1254 (2008).
Sugiura et al., "TRPV1 Function in Mouse Colon Sensory Neurons Is Enhanced by Metabotropic 5-Hydroxytryptamine Receptor Activation," *The Journal of Neuroscience*, 24(43): 9521-9530 (Oct. 27, 2004).

(56) References Cited

OTHER PUBLICATIONS

Tominaga et al., "The Coned Capsaicin Receptor Integrates Multiple Pain-Producing Stimuli," *Neuron,* 21(3): 531-543 (Sep. 1998).
Varga et al., "Relative Roles of Protein Kinase A and Protein Kinase C in Modulation of Transient Receptor Potential Vanilloid Type 1 Receptor Responsiveness in Rat Sensory Neurons In Vitro and Peripheral Nociceptors In Vivo," *Neuroscience,* 140(2): 645-657 (2006).
Winter et al., "Functionally important amino acid residues in the transient receptor potential vanilloid 1 (TRPV1) ion channel—an overview of the current mutational data," *Molecular Pain,* 9(30): 1-29 (2013).
Wolfe et al., "A Herpes Simplex Virus Vector System for Expression of Complex Cellular cDNA Libraries," *Journal of Virology,* 84(14): 7360-7368 (Jul. 2010).
Yokoyama et al., "Gene Therapy for Bladder Overactivity and Nociception with Herpes Simplex Virus Vectors Expressing Preproenkephalin," *Human Gene Therapy,* 20(1): 63-71 (Jan. 2009).
Yokoyama et al., "Effects of Herpes Simplex Virus Vector-Mediated Enkephalin Gene Therapy on Bladder Overactivity and Nociception," *Human Gene Therapy,* 24(2): 170-180 (Feb. 2013).
Zhang et al., "Activation of CaMKII and ERK1/2 contributes to the time-dependent potentiation of $Ca^{2+}$ response elicited by repeated application of capsaicin in rat DRG neurons," *Am. J. Physiol. Regul. Integr. Comp. Physiol.,* 300(3): R644-R654 (2011).

\* cited by examiner

TRPV1 MODULATORY GENE PRODUCT THAT AFFECTS TRPV1-SPECIFIC PAIN BEHAVIORAL RESPONSES IDENTIFIED IN A FUNCTIONAL SCREEN OF AN HSV-BASED CDNA LIBRARY

CROSS-REFERENCE TO RELATED APPLICATIONS

This patent application is a continuation of U.S. patent application Ser. No. 14/690,038, which claims the benefit of U.S. Provisional Patent Application 61/980,925, filed Apr. 17, 2014. The entire contents of each of these prior applications are incorporated herein in their entirety.

STATEMENT REGARDING FEDERALLY SPONSORED RESEARCH AND DEVELOPMENT

This invention was made with Government support under Grant Number DK044935 awarded by the National Institutes of Health. The Government has certain rights in this invention.

BACKGROUND OF THE INVENTION

Chronic pain represents a major cause of morbidity, significantly impairing quality of life and imposing a substantial financial and healthcare burden. The wide distribution of a limited range of neurotransmitters, receptors, and ion channels in the nervous system makes it difficult to selectively target pain-related pathways using drugs that are administered systemically. As a result, tolerance, abuse and deleterious side-effects limit the use of all currently available therapeutics.

We have previously used replication-defective HSV-based gene therapy vectors to deliver inhibitory neurotransmitters or gene products that attenuate the action of pronociceptive molecules to primary neuronal afferents of the peripheral nervous system (PNS), thereby blocking nociceptive neurotransmission in a variety of pre-clinical pain models [Goss et al., 2001; Goss et al., 2002; Goss et al., 2011; Hao et al., 2006; Hao et al., 2009; Miyazoto et al., 2010; Srinivasan et al., 2008; Wilson et al., 1999; Yokoyama et al., 2009] and more recently in patients [Fink et al., 2011)].

The transient receptor potential cation channel subfamily V member 1 (TRPV1) is one of 28 members of the transient receptor potential (TRP) non-selective cation channel superfamily and an important regulator of primary afferent nociceptive activity and pain signaling [Caterina & Julius, 2001]. TRPV1 can be induced by binding of the agonist capsaicin, as well as by protons and temperatures above 42° C. [Caterina et al., 1997; Tominaga et al., 1998]. TRPV1 has been documented to contribute to the chronic pain state in patients with arthritis, cancer, cystitis, diabetic neuropathy and post-herpetic neuralgia [Brederson et al., 2013; Bohlen & Julius, 2012; Roberson et al., 2011]. TRPV1 is primarily localized to the surface of small unmyelinated C-fibers that are thought to be the primary nociceptors as TRPV1 levels have been associated with thermal hyperalgesia (TH) in inflammatory and neuropathic pain models [for review see Winter et al., 2013].

Over the last decade, a number of gene products have been identified that modulate TRPV1 activity via phosphorylation of residues within the cytoplasmic domains of TRPV1 that assist in sensitization of the receptor. These products include calcium/calmodulin-dependent kinase (CamKinase-II) [Price et al., 2005; Zhang et al., 2011], protein kinase A (PKA) [Lee et al., 2012; Suguira et al., 2004: Varga et al., 2006] and the epsilon isoform of protein kinase C (PKCe) [Hucho et al., 2012]. TRPV1 activity is also modulated in the opposite manner (i.e. desensitization) via dephosphorylation of residues located in the cytosolic domains of the receptor. An established example of a desensitizing molecule is calcineurin, a $Ca^{2+}$-calmodulin-dependent serine/threonine protein phosphatase, also known as Protein Phosphatase 2B (PP2B) [Chaudhury et al., 2011; Jeske et al., 2006; Mohapatra & Nau, 2005; Por et al., 2010].

BRIEF SUMMARY OF THE INVENTION

The invention provides for the use of a novel pain inhibitor gene and cDNA encoding a product, PP1α, that is specific to TRPV1 as a potential pain gene therapy. The PP1α cDNA was identified in a screen of a cDNA library derived from PC12 cells differentiated with NGF and expressed from a replication-competent HSV vector that also expresses two copies of the TRPV1 gene.

When expressed from replication-defective HSV, the PP1α product of the identified cDNA can target nocifensive behaviors associated with TRPV1 but not TRPM8 or TRPA1, attesting to the specificity of this gene product. The TRPV1 specificity of PP1α is novel and crucial for a gene therapy approach to treating chronic pain as both TRPM8 and TRPA1 are involved in a variety of important responses including touch, cold and other sensations that are preferably left unaltered by the treatment. Thus, using a gene product like PP1α that specifically targets TRPV1-activated pain provides a layer of safety by decreasing unwanted side effects. For example, patients treated with the PP1α gene therapy approach will still be able to actively sense cold stimuli so that they can respond to a cold stimulus that would result in acute pain.

We have expressed PP1α from a replication-defective HSV vector that is deleted for the essential ICP4 and ICP27 genes. We have shown that HSV-based expression of PP1α, similar to that of a dominant-negative version of TRPV1 referred to as Poreless (PL), can reduce TRPV1 sensitization by the agonist capsaicin in rat primary DRG neurons in vitro as measured by calcium imaging and capsaicin-induced thermal pain responses in vivo following vector injection into the footpads of Sprague-Dawley male rats. In addition, we have shown that HSV vector-expressed PP1α did not alter the function of other TRP channels such as TRPM8 following menthol or icilin induction in the cold ramp test, or TRPA1 in the formalin pain test.

PP1α is the first and only product tested preclinically as a gene therapy for pain that specifically targets TRPV1-associated pain and does not affect the normal TRPM8 and TRPA1 responses.

The PP1α replication-defective HSV vector can also ameliorate bladder pain in rats in which another TRPV1 agonist, Resiniferatoxin (RTx), is used to activate the pain response. PP1α gene therapy may also interfere with other types of pain such as arthritis pain, VZV-associated Post-Herpetic Neuralgia (PHN) pain, bone cancer pain, the spinal nerve ligation (SNL) or chronic constriction injury (CCI) models of neuropathic pain, and complete Freund's adjuvant (CFA)-induced inflammatory pain.

BRIEF DESCRIPTION OF THE SEVERAL VIEWS OF THE DRAWING(S)

FIG. 1 schematically depicts HSV vectors and cDNA library screening protocol for TRPV1 inhibitors. (A) Virus vectors. HSV KOS-BAC contains the BAC sequences that contain the E. coli origin and a chloramphenicol resistance gene for selection in bacteria. TTA BAC contains: two copies of the TRPV1 gene, under control of the TK early gene promoter that will be active when the virus replicates, were inserted into the UL23 and UL41 gene loci within the KOS-BAC genome; the Gateway sequences were inserted into the joint region; the PC12 cell cDNA library was introduced into the gateway cassette under the control of the HCMV promoter that will allow robust expression of the genes within the library prior to expression of TRPV1. (B) The library was generated from differentiated and non-differentiated PC-12 cells (representing genes ranging in size from ~0.5-3 Kb) was inserted into the TTA BAC via a Gateway recombination LR clonase reaction. (C) The TTA library was screened (~500K PFU) by infecting Vero cells followed by the addition of 0.5 μM of the TRPV1 agonist capsaicin. Only viruses making a product that counteracts the capsaicin induction of TRPV1 will allow virus to replicate and survive. Following a second screen 25/46 isolates remained. cDNAs were made of the 25 candidates, re-introduced into the TTA BAC and re-screened in the presence of capsaicin. The lone remaining isolate from the final screen was sequenced and showed direct homology to the gene product protein phosphatase 1-α or PP1α.

Figure 2:
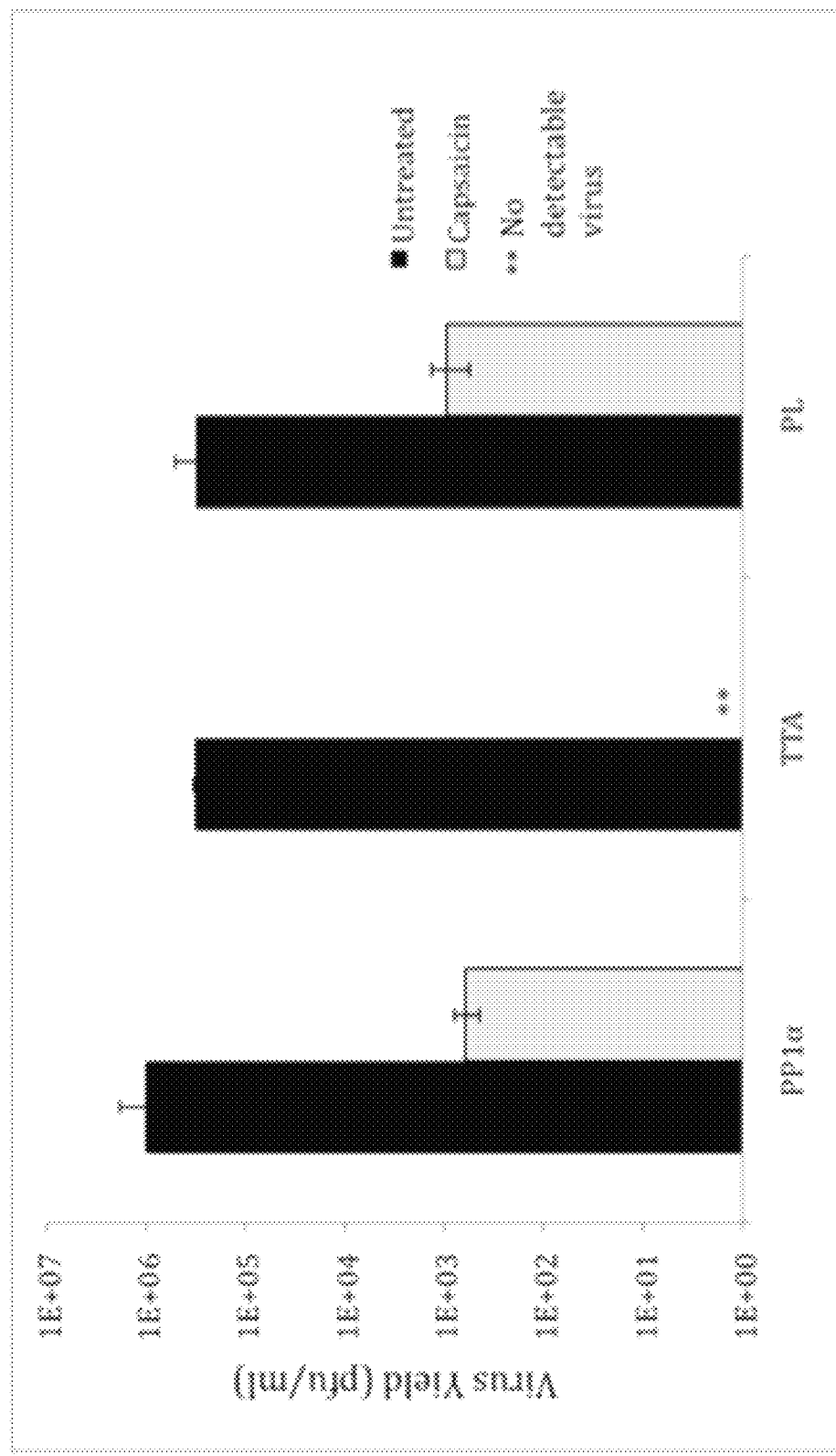
Figure 3:
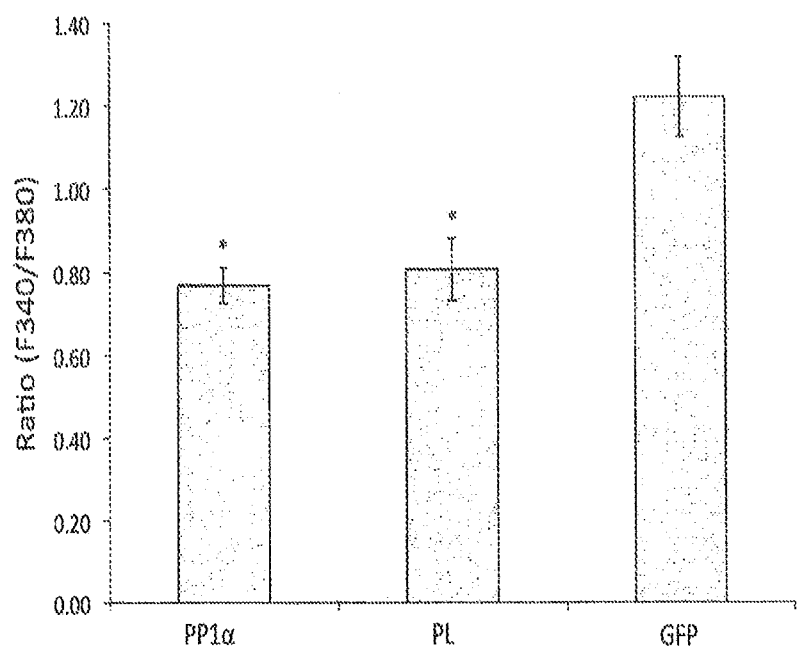
Figure 4:
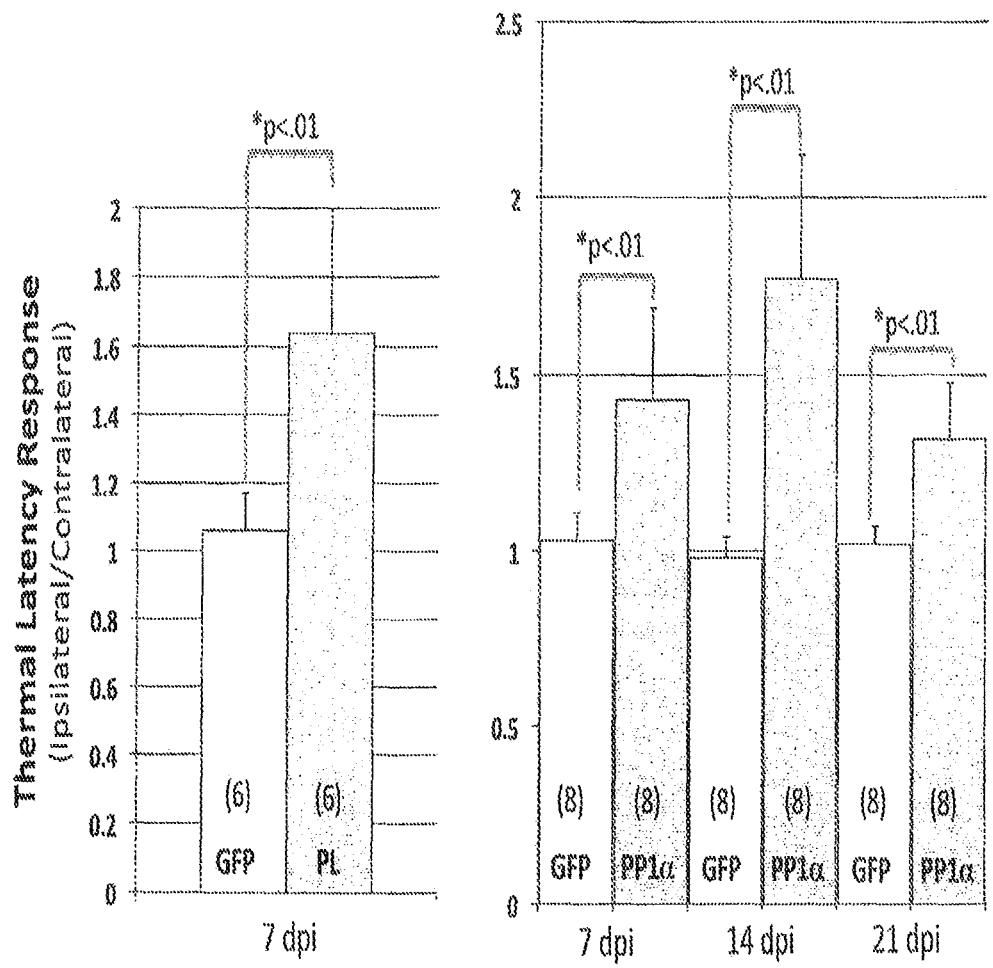
Figure 5:
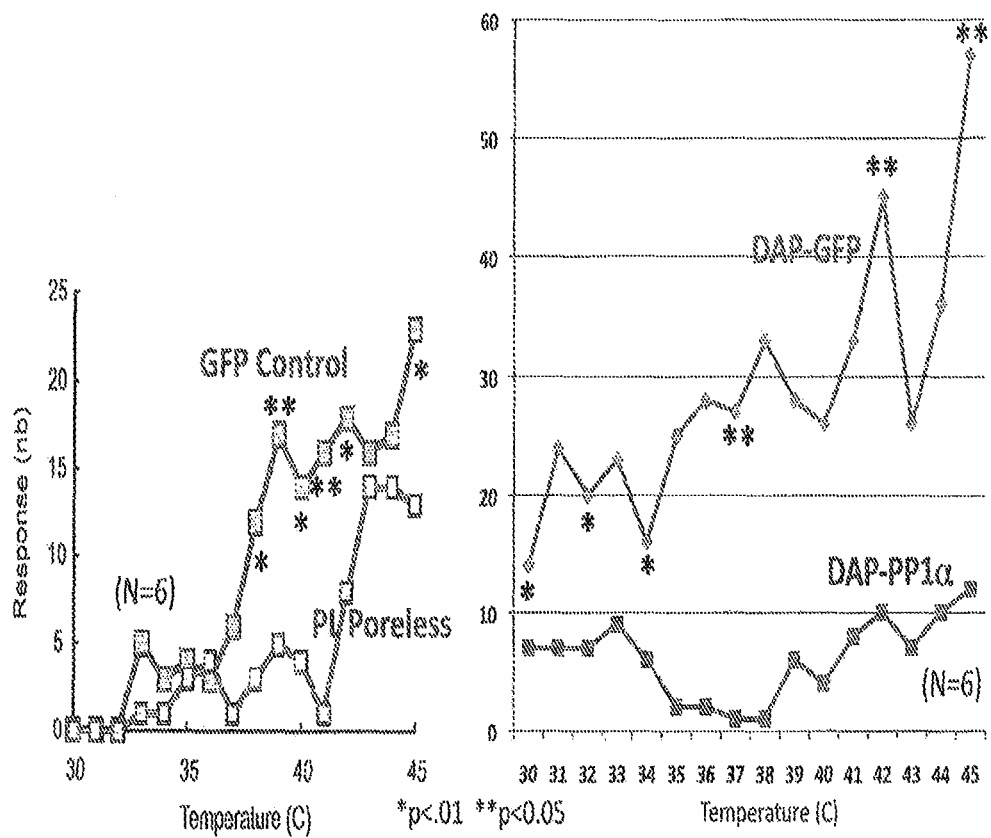

FIG. 2 presents data verifying the ability of the PP1α cDNA to enable virus replication in the presence of capsaicin. In order to verify that the PP1α isolate was working and show that its actions were through down-regulating capsaicin activation of the TRPV1 receptor, we compared the growth of the PP1α isolate with the TTA BAC that lacks the cDNA library (negative control), and to a positive control virus that contains a known modulator of TRPV1 called Poreless (PL), a dominant-negative mutant form of TRPV1 that when expressed poisons the action of the wild-type TRPV1. We had previously used the Poreless-TRPV1 expressing virus to verify that our capsaicin screening procedure was valid in comparison to the TTA BAC virus. Cells infected with the 3 viruses (PP1α, TTA and PL) were either left untreated to show maximum levels of virus replication (black bars), or treated with 0.5 μM capsaicin (grey bars). The TTA negative control virus replicated in the absence of capsaicin but no virus was detected when 0.5 μM capsaicin was added, as seen during the screening process. The PL positive control virus in the presence of capsaicin was able to replicate to about 50% of the levels seen without capsaicin similar to that observed when we first tested the entire screening process. Finally, the PP1α virus showed similar levels of replication to that of the PL positive control virus in the presence of 0.5 μM capsaicin, verifying what we had observed in the screening process.

FIG. 3 presents data demonstrating the ability of HSV vector expressed PP1α to alter TRPV1 activity in fetal dorsal root ganglia neurons using calcium imaging. Fetal DRG neurons were isolated from day e15 rat embryos and cultured in Neurobasal Medium supplemented with B27 and NGF. At 1-2 weeks post-plating, cultures were infected with vector replication-defective HSV vectors expressing GFP (negative control), poreless (PL) positive control, or the PP1α test vector. Calcium imaging was assessed at 3 hours post-infection in the presence of 0.5 μM capsaicin using Fura-2, a cell-permeable fluorescent $Ca^{2+}$ indicator to measure the influx of $Ca^{2+}$. The data in the bar graph depicts the Fura-2 Ratio (F340/F380) which is proportional to the concentration of intracellular calcium present within the DRG neurons. The results represent the average of multiple measurements from DRG neurons infected with the three viruses. Both poreless and PP1α expression resulted in statistically significant reductions in the levels of intracellular calcium, that supports their augmentation of the capsaicin induction of the TRPV1 channels.

FIG. 4 presents data demonstrating the inhibition of chronic pain signaling using a vector expressing PP1α protein or Poreless TRPV1. Male Sprague-Dawley rats were injected subcutaneously into the right rear hind paw with $1\times10^8$ pfu of either a control vector (vHG, N=6) or a vector expressing a poreless TRPV1 (PL, N=6) or with $1\times10^7$ pfu of either a control vector (GFP, N=6) or PP1α-expressing vector (N=6). One, two and three weeks later, thermal response was assessed by placing each animal into a plexiglass enclosure on a glass surface maintained at 30° C. (Hargreaves apparatus). After a 15 min accommodation period, a light beam was focused onto the mid-plantar area of each hind paw and the amount of time it took each animal to move its paw from the heat source measured. The average of three trials per hind paw for each animal was used to determine each animal's thermal response. Values represent the ratio of response between the ipsilateral (injected) and contralateral (non-injected) paw. SPSS stats package determined one-way ANOVA $*p<0.01$.

FIG. 5 presents data demonstrating the inhibition of capsaicin induced thermal allodynia in rats by footpad injection of replication-defective vectors expressing Poreless TRPV1 or PP1α. Male Sprague-Dawley rats were injected subcutaneously into the right rear hind paw with $1\times10^8$ pfu of either a control vector (GFP, N=6) or the poreless TRPV1 (PL, N=6) or with $1\times10^7$ pfu of either a control vector (GFP, N=6) or PP1α-expressing vector (PP1α, N=6). One week later, capsaicin (10 mM in 50% ethanol) was applied to the plantar surface of the right hind paw to lower the thermal pain threshold. Animals were placed on a dynamic hot place where temperature increased from 30° C. to 45° C. over a 15 minute period. During each degree interval the total number of pain-related behaviors (licking, paw withdrawals) for the injected ipsilateral paw were counted and plotted as the number of responses. Both PL and PP1α alter the thermal allodynia behavioral response to capsaicin.

FIG. 6 presents data demonstrating that Poreless TRPV1 and PP1α HSV vectors have no effect on cold-induced pain. Since noxious cold temperature is transduced primarily by TRPM8 receptors, our poreless TRPV1 vector should not interfere with its function. Male Sprague-Dawley rats were injected subcutaneously into the right rear hindpaw with $1\times10^8$ pfu of either a control vector (GFP, N=6) or the poreless TRPV1 (PL, N=6) or with $1\times10^7$ pfu of either a control vector (GFP, N=6) or PP1α-expressing vector (PP1α, N=6). 7-10 days later, animals were placed on a dynamic cold plate where temperature decreased from 30° C. to 4° C. over a 15 minute period. Additionally, with the PP1α vs. GFP control, a solution of 5% menthol was placed on the right hindpaw prior to placing the rat on the cold ramp. During each degree interval the total number of pain-related behaviors (licking, paw withdrawals) for the injected ipsilateral and non-injected contralateral were counted and the total number of licks and withdrawals for the injected hindpaw are plotted. Neither PL or PP1α vectors had any effect on the cold-related behavioral responses in the rats compared to the GFP control-injected rats even in presence of TRPM8 agonist menthol.

FIG. 7 presents data demonstrating that HSV vector-mediated PP1α expression has no effect on TRPA1 nociception behavior evaluated using the formalin footpad test. Male Sprague-Dawley rats were injected subcutaneously into the right rear hindpaw with 1×10$^7$ pfu of either a control vector (GFP, N-6) or PP1α-expressing vector (PP1α, N=6). 7-10 days later, a dilute solution of formalin (2.5%) was injected subcutaneously in the plantar aspect of the same foot that had received the viral inoculation, and the rats then placed into a 48-27-20 cm plastic box positioned over a mirror tilted at a 45° angle. Beginning 30 s after the injection of formalin, and once every 10 min thereafter, nocifensive behaviors were recorded by a blinded observer for 3 min. A weighted pain score was derived based on the amount of time the animal exhibited each behavior during the 3-min period of observation [0=plantar surface of foot flat against surface; 1=foot cupped with only toes touching surface; 2=lifting of foot from surface; 3=complete withdrawal of foot with licking]. The weighted pain score was plotted against time, and compared between control and treatment groups using a one-way ANOVA.

Figure 8:
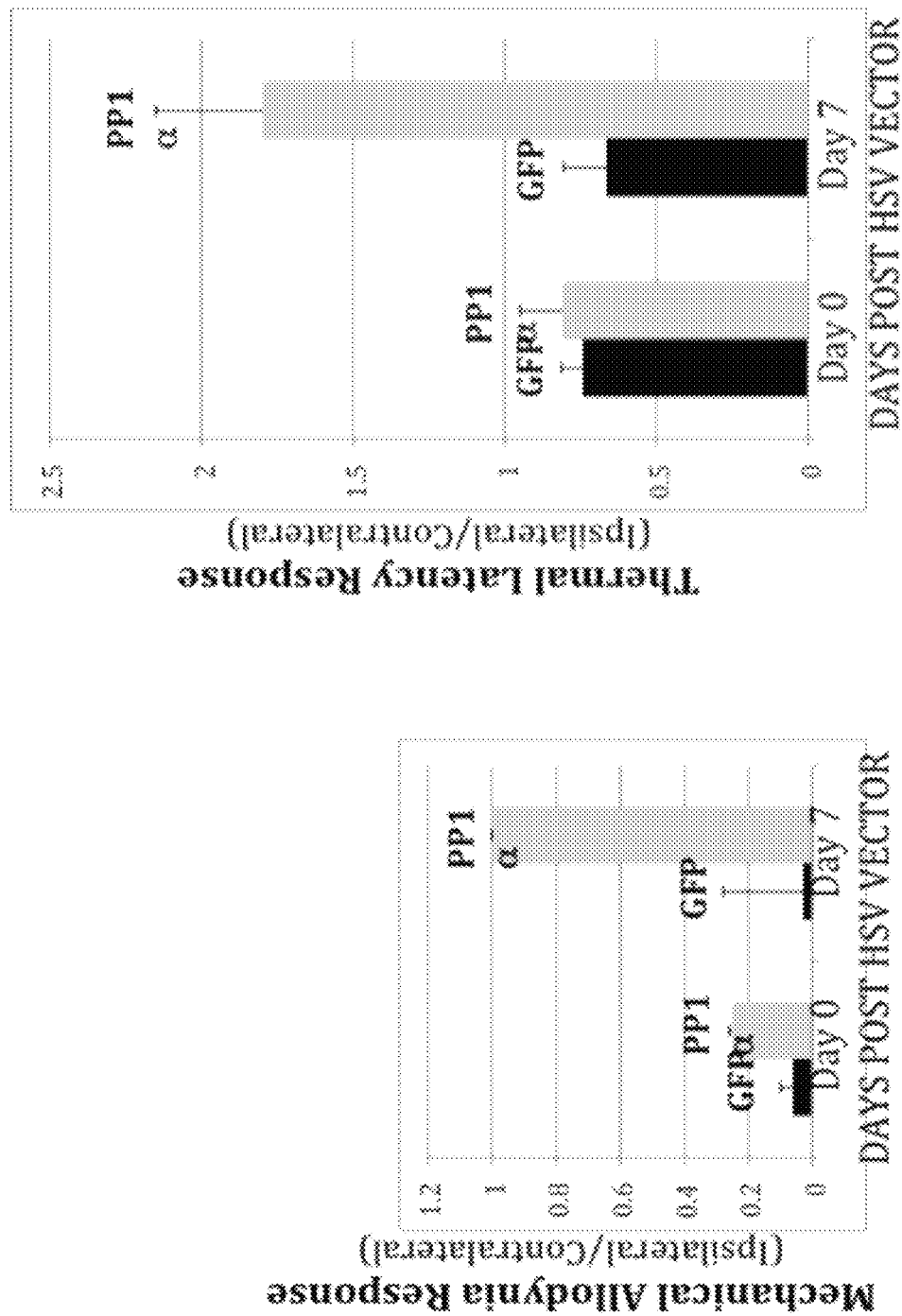

FIG. 8 presents data demonstrating that PP1α reduces both thermal and mechanical nocifensive behavioral responses in the rat model of VZV-induced PHN. Baseline mechanical allodynia (MA) and thermal hyperalgesia (TH) nocifensive responses were measured in ten male Sprague Dawley rats using the von Frey hair up-down method (MA) or the Hargreaves (TH) apparatus. Rats were then injected into their right hindpaws with MeWo infected with 10$^5$ pfu VZV strain pOka (parent of Oka, similar to VZV vOka vaccine strain). At 7 and 14 days post VZV, MA and TH behaviors were measured. Next, on DAY-0 the rats were injected into the same hindpaws with 10$^7$ pfu of either the control GFP-expressing replication-defective HSV vector or the PP1a-expressing vector. At DAY-7, rat MA and TH behaviors were assessed. All behavioral scores are plotted as the average response ratio for the ipsilateral injected hindpaw to the contralateral un-injected hindpaw. VZV-PHN mechanical and thermal nocifensive behaviors were observed at Day 0, however, only the control GFP-expressing animals retained these responses at Day 7 while the PP1α-expressing vector dramatically reduced both MA and TH nocifensive behaviors in a statistically significant manner. The average paw withdrawal latency time for the uninjected non-inured rats ranged from 7-10 seconds while those for the VZV-injected/PP1α vector injected rats ranged from 13-25.

Figure 9:
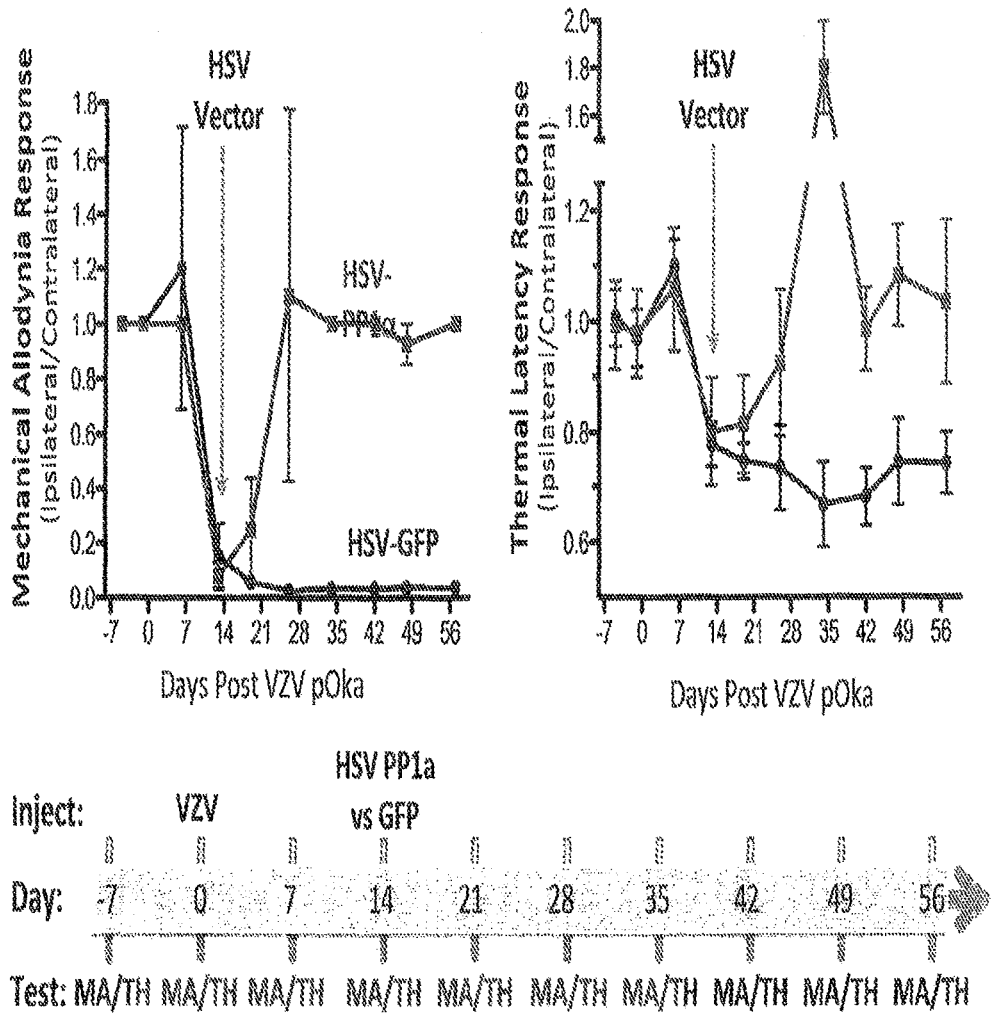

FIG. 9 presents data demonstrating that PP1α reduces both thermal and mechanical nocifensive behavioral responses in the rat model of VZV-induced PHN over 6 weeks post injection of PP1α HSV vector compared to control GFP vector. Baseline MA and TH nocifensive responses were measured in ten male Sprague Dawley rats. Rats were then injected into their right hindpaws with MeWo cells infected with 10$^5$ pfu of VZV strain pOka. At 7 and 14 days post VZV, MA and TH behaviors were measured where all rats displayed pain. Next, on DAY-15 the rats were injected into the same hindpaws with 10$^7$ pfu of either the control GFP-expressing HSV vector or the PP1α-expressing vector. At weekly intervals, rat MA and TH behaviors were assessed. All behavioral scores are plotted as the average response ratio for the ipsilateral injected hindpaw to the contralateral un-injected hindpaw. VZV-PHN mechanical and thermal nocifensive behaviors were observed by 14 days post VZV pOka. However, only the rats injected with the control GFP-expressing vector retained these responses (7 days post HSV vector injection and later) while the PP1α-expressing vector dramatically reduced both MA and TH nocifensive behaviors in a statistically significant manner. Even at 6 weeks following HSV vector injection, the PP1α vector continues to block the painful behaviors in the PHN rats at statistically significant levels.

Figure 10:
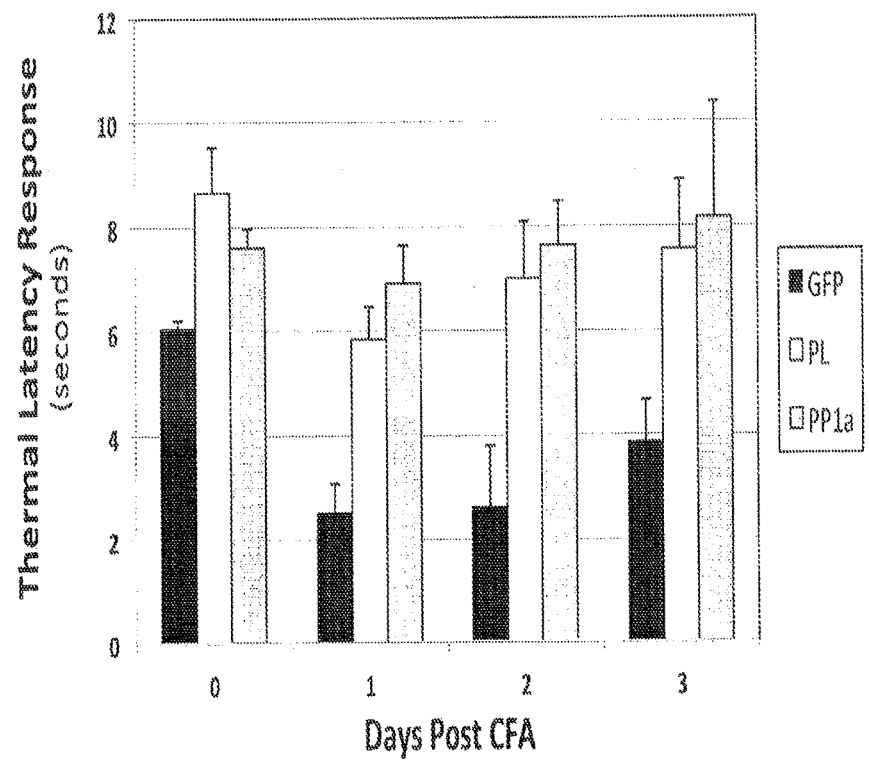

FIG. 10 presents data demonstrating Inhibition of CFA-induced nocifensive behavior using an HSV vector expressing PP1α and Poreless-TRPV1. Male Sprague-Dawley rats (200-250 g) were assessed for baseline thermal behavior by placing each rat into a plexiglass enclosure on a glass surface maintained at 30° C. (Hargreaves apparatus). After a 15 min accommodation period, a light beam was focused onto the midplantar area of each hind paw and the amount of time it took in seconds for each animal to move its paw from the heat source was measured. The average of three trials per hind paw for each animal was used to determine each animal's thermal response. Rats were then injected subcutaneously into the right rear hind-paw with 1×10$^8$ pfu of either a control vector (DAP-GFP, N=4), a vector expressing a PP1α (DAP-PP1α, N=4), or vector expressing a Poreless-TRPV1 (DAP-PL, N=4). Three weeks later, thermal response was again assessed and the average and standard deviation of the thermal response times (in seconds) shown for the injected right hind-paw as time point 0 days post CFA injection. After this Day 0 measurement, 100 μL of complete Freund's adjuvant (CFA) was injected into the right hind-paw as previously described (Goss et al., 2011) and the thermal response was again assessed at 1, 2 and 3 days post-CFA injection.

DETAILED DESCRIPTION OF THE INVENTION

In one aspect, the invention provides a herpes simplex virus (HSV) vector comprising an expression cassette, which comprises a nucleic acid sequence encoding PP1α. The vector backbone is preferably replication incompetent in vivo. For example, the HSV vector can be engineered to contain deletions and/or inactivating mutations of genes essential for viral replication in cells not otherwise complementing for such viral proteins. For example, a suitable HSV vector backbone can lack functioning ICP4 and ICP27 genes, as well as other genes (e.g., ICP0). Additionally, the HSV vector can be targeted to particular types of cells, such as neurons that are involved in the sensation of pain (e.g., C-fibers). Examples of replication-deficient and targeted HSV vectors, and their methods of production and replication are known in the art. See, e.g., U.S. Pat. Nos. 8,309,349, 8,003,622, 7,825,231, 7,531,167, 7,078,029, 6,261,552, 5,998,174, 5,879,934, 5,849,572, 5,849,571, 5,804,413, and 5,658,724; US patent application publication numbers 20020090382, 20070178069, 20070207124, 20080289058, 20090238807, and 20110213017, and international patent application publication numbers WO/2011/130749, WO/2008/143875, WO/2006/050211, WO/1999/061067, and WO/1999/006583, each of which is incorporated herein by reference.

Within the vector, preferably the nucleic acid sequence encoding PP1α is operably linked to a promoter sequence other than the native PP1α promoter. For example, the nucleic acid sequence encoding PP1α can be operably linked to a strong constitutive promoter, such as the hCMV1 major immediate-early (IE) gene promoter. For expression within neurons, it will be appreciated that the nucleic acid sequence encoding PP1α can be operably linked to a neuronal-specific promoter. For example, since PP1α inhibits TRPV1, within the inventive vector, the nucleic acid sequence encoding PP1α can be operably linked to the TRPV1 promoter, which will aid in confining expression of PP1α to cells which also express TRPV1. Alternatively, the nucleic acid sequence encoding PP1α can be operably linked to a non-neuronal promoter that provides long-lasting gene expression within neurons, such as the ubiquitin (Ub) promoter.

For use in the context of the present invention, preferably (a) the PP1α, (b) the genetic regulatory elements to which it is operably linked (e.g., its promoter) within the vector, and more preferably (c) both the PP1α and its genetic regulatory elements within the vector, are co-specific with the species of cells to which the vector is administered. Thus, for medical use in humans, preferably the PP1α, its promoter within the vector, and more preferably both, are human sequences.

It will be appreciated that the inventive HSV vectors can be propagated into a stock comprising numerous such vectors. Thus, the invention provides a stock comprising such vectors, which can have any suitable titer of vectors. Desirably, the stock has a titer of between about $10^8$ and about $10^{11}$ pfu/ml or greater.

The invention also provides a pharmaceutical composition comprising the vectors containing the nucleic acid sequence encoding PP1α as described herein, and a pharmaceutically-acceptable carrier. Any suitable carrier can be used, so long as it is compatible with the HSV vectors and also suitable for pharmaceutical use. Typically, such carriers are physiological saline solutions, which facilitate administration via skin prick, or via subdermal, intramuscular, or parenteral injection. However, other carriers (e.g., salves, creams, patches, and the like for transdermal administration) also can be used. For treating CNS conditions, carriers suitable for intracranial administration can be employed.

The invention also provides a method of treating pain within a mammal in need thereof. The method comprises administering a pharmaceutical composition comprising the vectors comprising an expression cassette, which comprises a nucleic acid sequence encoding PP1α, to the mammal in an amount and at a location sufficient to result in vectors within the composition to infect peripheral neurons associated with the sensation of pain. Within such neurons, the nucleic acid sequences encoding PP1α within the vectors are transcribed within the neurons to produce PP1α within the neurons. Typically, the mammal is human, but laboratory animal models (e.g., mice, rats, etc.), companion animals (e.g., cats, dogs, horses, etc.) or animals of zoological importance (apes and other primates, ungulates, antelopes, great cats, and other animals) or of agricultural importance (cattle, goats, sheep, swine, etc.) can also be treated in accordance with the inventive method. The method can also be used to mitigate the sensation of pain caused by exposure to capsaicin or resiniferatoxin (RTX). Without wishing to be bound by any particular theory, it is believed that the presence of PP1α within the neurons as a result of the inventive method antagonizes the activity of TRPV1 within the neurons. It is believed that the method is specific to pain mediated by TRPV1 (heat-related, capsaicin-induced, and associated with low pH), but does not mitigate pain associated with exposure to cold. In particular, it has been discovered that PP1α does not block TRPA1 or TRPM8 responses.

It will be recognized that, in carrying out the inventive methods, vectors other than those based on HSV can be used. For example, the vector can be derived from human or other mammalian adenoviruses, adeno-associated viruses, retroviruses, and the like. In some applications, plasmids, liposomes, and other non-viral vector systems alternatively can be employed. These vector systems, and their methods of construction, propagation, and formulation for pharmaceutical use, are known to persons of ordinary skill.

The following examples further illustrate the invention but, of course, should not be construed as in any way limiting its scope.

EXAMPLE 1

This example demonstrates the identification of a TRPV1 modulatory gene product from an HSV-based cDNA library screen for gene products that blocks capsaicin-induced TRPV1 activation and cell death, allowing HSV vector plaque formation.

We sought to test the hypothesis of whether cellular modulators of TRPV1 activation exist to control the appearance of long-term pain, a function that represents a viable target for down-regulation during the transition from acute to chronic pain. To this goal, we employed an HSV-based cDNA library expression screen methodology based on a previous screening method [Srinivasan et al., 2007] designed to identify cellular regulators of TRPV1 activation that may control the occurrence of TRPV1-related nocifensive responses.

Our library screen was based on the observation that TRPV1 expression in Vero cells, commonly used for HSV growth, caused rapid cell death via calcium influx in the presence of capsaicin, suggesting that plaque formation by an HSV-based TRPV1 expression vector in the presence of capsaicin would only occur if the vector also expressed an antagonist of TRPV1 activation. To develop this system, we engineered a bacterial artificial chromosome (BAC)-based HSV-1 genome in *E. coli* to contain: (i) the cDNA for TRPV1 in place of the viral thymidine kinase (tk, UL23) gene and the UL41 virion host shut-off gene (vhs, UL41) under control of the HSV early (β) tk gene promoter; (ii) a Gateway (GW) recombination cassette flanked by the hCMV1 major IE gene promoter and bovine growth hormone (bGH) polyA region in place of the internal repeat (joint) region of the virus; and (iii) a second antibiotic resistance gene (ampicillin-resistance) inserted between UL55 and UL56 (FIG. 1A); the region between UL37 and UL38 contains a chloramphenicol resistance gene associated with the BAC elements. The presence of both ampicillin and chloramphenicol during vector growth in *E. coli* prevents the amplification of defective recombinants that have lost either region between the TRPV1 genes on the circular BAC genome (UL38-UL55 and UL56-UL37) due to recombination between the 2 copies of the TRPV1 gene. BAC DNA from thus selected *E. coli* was transfected into Vero cells and infectious virus was harvested and titered as plaque forming units (pfu). In the presence of capsaicin, plaque formation was substantially reduced but not completely eliminated (1 plaque/10,000 input pfu), an acceptable background level for use in the cDNA library screen.

Figure 6:
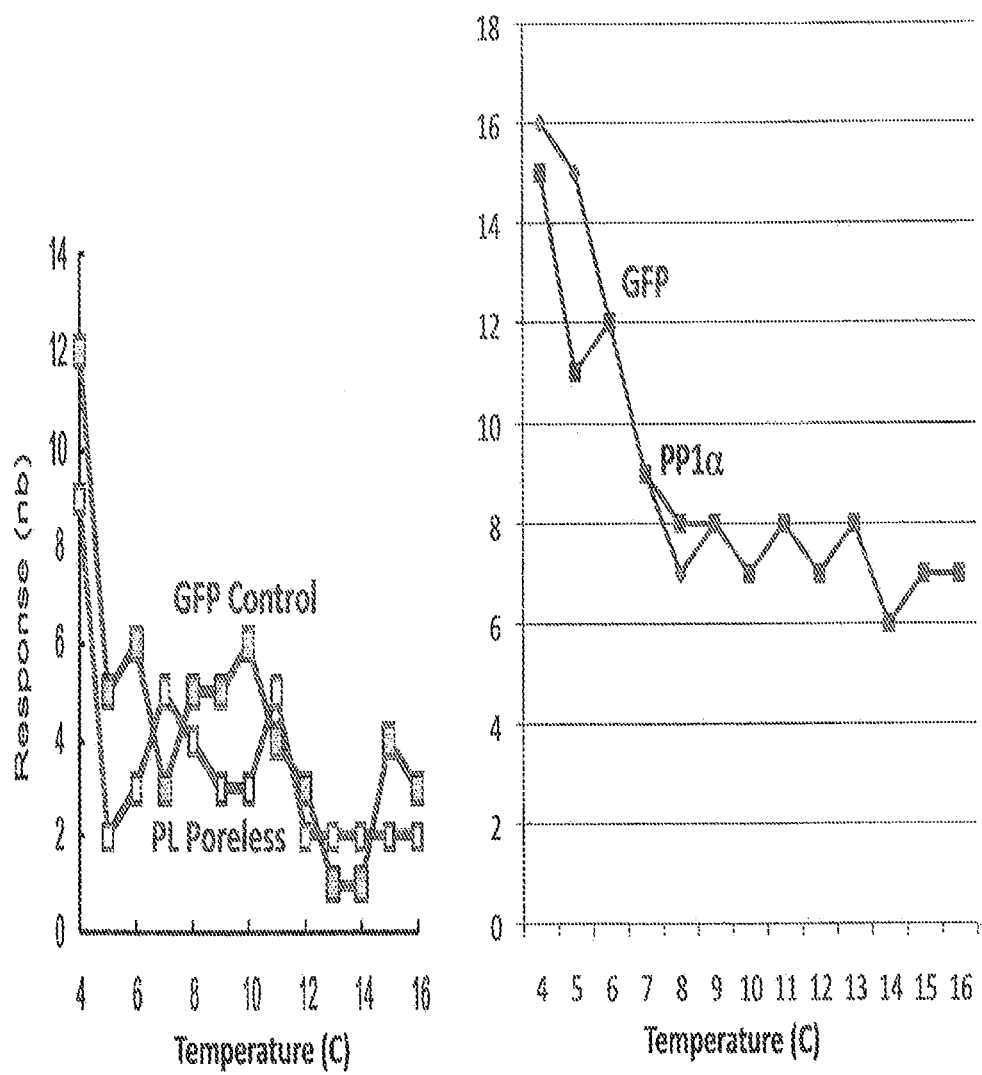

Next we recombined a previously described entry cDNA library [Wolfe et al., 2010] derived from a mixture of NGF-differentiated and undifferentiated PC12 cells into the GW locus of the double-TRPV1/amp (TTA) BAC and converted bulk recombinants into infectious virus (FIG. 1B) with insert sizes ranging from 400 bp to ~3 kb (FIG. 1B). Approximately 500,000 pfu of virus were screened in the presence of 1 mM capsaicin (FIG. 1C) and a total of 46 candidate plaques were isolated, amplified on Vero cells and retested for capsaicin-resistance. Upon rescreening, approximately 50% of the isolated plaques retained a capsaicin-resistant phenotype. The cDNA inserts from candidates that were positive upon rescreening were then PCR amplified, introduced into a new TTA BAC backbone and retested for capsaicin resistance to confirm that the cDNA were not isolated from false negatives. One candidate clone consistently demonstrated the ability to rescue virus replication in the presence of capsaicin and sequencing of this candidate insert identified the gene as the full-length PP1α cDNA. Of note, this is the first observation within the literature in which TRPV1 activity is altered by the expression of the PP1α phosphatase, although the PP2B phosphatase calcineurin has been previously shown to have the ability to desensitize capsaicin-induced TRPV1 [Chaudhury et al., 2011; Docherty et al., 1996; Jeske et al., 2006; Mohapatra & Nau, 2005; Por et al., 2010].

We then tested the ability of the PP1α-TTA recombinant virus to replicate in the presence of capsaicin with that of a positive control virus [Poreless (PL)-TTA] and a negative (TTA) control vector that is identical to the PP1α-TTA except that it lacks any inserted gene. If the PP1α-TTA expressing PP1α acts to diminish TRPV1 activation in the presence of the agonist capsaicin, then it will enable the virus to grow to levels approaching that seen in the absence of capsaicin. This level for the PP1α-TTA recombinant should be similar to that seen with the PL-TTA positive control vector, since poreless TRPV1 acts in a dominant-negative manner to inhibit TRPV1 activity [Srinivasan et al., 2007]. The negative control vector should not be able to reduce the capsaicin induced sensitization of TRPV1, and thus one should see calcium influx and cell death so that the TTA negative control can not replicate. Vero cells were infected with low amounts of virus (MOI=0.01) and virus yield was measured 48 hours later. TTA virus produced no infectious progeny while PP1α-TTA replicated with an efficiency similar to PL-TTA, both yielding approximately 3,000 pfu compared to $0.5\text{-}1\times10^6$ pfu produced in the absence of capsaicin (FIG. 2). The yields in the absence of capsaicin were comparable between the three viruses, indicating that expression of PP1α and PL from the TTA vectors did not universally improve virus yield.

Having now confirmed that PP1α acts similarly to PL upon capsaicin-induced sensitization of TRPV1, we tested of the function of PP1α in neurons both in vitro and in vivo using a non-replicating HSV vector. Thus, we engineered 3 new vectors containing the strong hCMV IE promoter driving PP1α, PL or eGFP cDNA inserted into the essential HSV ICP27 IE gene locus in a vector backbone that was deleted for the essential ICP4 IE gene. These replication-defective vectors can only be propagated on Vero cells engineered to complement the deleted ICP4 and ICP27 essential IE genes in trans [Marconi et al., 1996], yet they readily express high-levels of the transgene in non-complementing cells, including neurons. As an in vitro test of the activity of the PP1α candidate gene product to modify capsaicin-induced TRPV1 activity, we compared the abilities of the replication-defective PP1α, PL and eGFP vectors to block the capsaicin-induced calcium influx in primary rat fetal DRG neurons in culture using Fura-2, a cell-permeable fluorescent $Ca^{2+}$ indicator [Zhang et al., 2011]. Capsaicin addition to the fetal DRG cultures should activate the opening of the TRPV1 channel, causing an influx of $Ca^{2+}$ into the neurons which will lead to a increase in Fura-2 fluorescent signal, as observed for cultured DRGs that had been infected with the eGFP control virus (FIG. 3). However, if the candidate gene reduces capsaicin-induced TRPV1 activity, one should observe a decrease in the Fura-2 fluorescent signal, as observed with the positive control virus expressing the PL protein that is known to interfere with TRPV1 function following capsaicin treatment (FIG. 3). Finally, the PP1α-expressing vector, like the PL positive control vector, showed significantly reduced calcium uptake in the presence of capsaicin compared with the eGFP control vector (p=0.01).

The next goal was to determine whether PP1α expressed from the vector alters nociceptor signaling via TRPV1 and if other TRP channels would be affected as well by this phosphatase. Because TRPV1 has been well-documented to be involved in thermal pain responses such as thermal hyperalgesia (TH), we first tested the ability of the non-replicating PP1α, PL (positive control) or eGFP (negative control) vectors to increase paw withdrawal latency using a Hargreaves apparatus [Hargreaves et al., 1988; Goss et al., 2011]. Male Sprague-Dawley rats were injected with vector into the right footpad (n=6-8) and the TH nociceptive responses were recorded at 7-21 days with an average of three trials per hind paw. Each animal's thermal response was expressed as a ratio between the contralateral (non-injected) to ipsilateral (injected) paw, so that each rat acted as its own internal control. If the vector-expressed gene alters the TH response and the animal is not sensing the thermal-induced pain as readily, then the TH response for the vector-injected ipsilateral paw increases in comparison to the un-injected paw and the TH response ratio will be >1. However, if the gene product has no effect on thermal-induced pain, then both paws will display a similar response to heat and the response ratio will be ~1. The positive control PL vector produced a 1.6-fold increase in paw withdrawal latency compared to the eGFP control vector at 7 days post vector injection (FIG. 4) and the PP1α-expressing vector yielded a 1.4-1.7× increase in paw withdrawal compared to the eGFP control vector over the period from 1-3 weeks post vector injection (FIG. 4), again showing that the PP1α gene candidate acted in a manner similar to the TRPV1 modulatory gene poreless (PL).

The next step was to confirm the role of PP1α in capsaicin-induced desensitization of TRPV1 as we had observed in the screen itself as well as in the tests of vector replication (FIG. 2) and calcium imaging (FIG. 3) in response to the addition of the capsaicin TRPV1 agonist. To assess this, we compared rats again injected into their right hindpaw with the 3 vectors on a dynamic hot plate where temperature increased from 30° C. to 45° C. over a 15 minute period following injection of 10 mM capsaicin to the plantar surface of the injected ipsilateral paw. During each degree-minute interval, the total number of pain-related behaviors (licking, paw withdrawals) for the injected ipsilateral paw were counted and plotted. If the vector-expressed gene works via modulating TRPV1 activity, it should display reduced numbers of nocifensive painful responses compared to the control vector, and this difference should be even more pronounced at temperatures >42° C. since the TRPV1 channel is highly activated by elevated temperatures, especially in the presence of agonist. The PL positive-control vector reduced the number of pain-related responses compared with the eGFP control vector as the temperature of the heat ramp increased approaching 42° C. (FIG. 5). While the differences were less significant at temperatures >42° C., the PP1α-expressing vector showed significant differences with the eGFP vector in the number of painful responses out to 45° C., attesting to the ability of the PP1α-expressing vector to control the thermal nociceptive response that is specific for capsaicin-induced pain sensitivity via TRPV1, confirming that PP1α is acting by modulating the activity of TRPV1.

Since we had performed both in vitro and in vivo testing of the ability of HSV vector-expressed PP1α to modify the activity of the TRP channel TRPV1 in models of thermal pain with and without capsaicin induction, we wished to test whether vector-expressed PP1α modulates other TRP receptors such as TRPM8 and TRPA1. To assess whether PP1α can modulate TRPM8 activity, we performed a cold ramp assay that is identical to the heat ramp except that the rats injected into the right footpad with the 3 vectors (GFP, PL, and PP1α; n=6 rats/vector group) are subjected to temperatures that decrease over the 15-minute period from 20° C. to 4° C. at a rate of 1° C. per minute. Again, like the heat ramp assay, the number of painful responses (withdrawal and licking of the ipsilateral hindpaw) was recorded at each temperature during the drop in cold ramp temperature. In this assay, neither the PL positive-control vector nor the PP1α gene vector (FIG. 6) displayed any difference from the eGFP negative-control vector.

We also performed the exact same cold ramp test following the injection of either menthol or icilin into the plantar surface of the vector-injected ipsilateral footpad as was done with capsaicin in the heat ramp assay. Neither the PL nor PP1α vectors showed any differences from the eGFP vector in the pain responses to injection of these TRPM8 agonists in the context of decreasing temperatures from normal room temperature to 4° C. (data not shown). These negative results demonstrate that PP1α does not modulate TRPM8 activity or desensitization, verifying that it shows functional specificity for the TRPV1 TRP channel. A sole report exists in the literature that uses a drug inhibitor of PP1 (Okadaic Acid) to suggest that PP1 may be involved in TRPM8 desensitization [Premkumar et al., 2005]. However, as acknowledged in the report, it is entirely possible that the concentration of the inhibitor employed actually inhibited PP2A that is also sensitive to the drug. Thus, this does not conflict with our results in the rat cold ramp model using either menthol or icilin as agonists of TRPM8.

Figure 7:
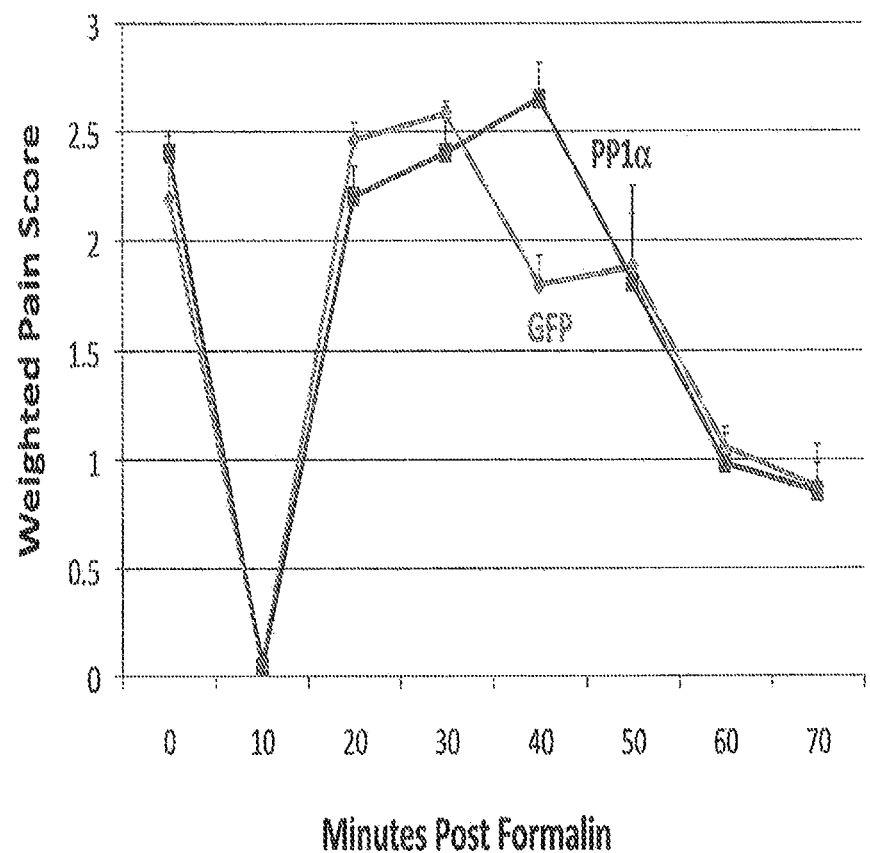

Another TRP involved in sensation and the pain response is the TRPA1 channel. To examine whether PP1α can modulate TRPA1 activity, we tested the three vectors in the formalin footpad test where the late phase inflammatory pain response to formalin injection into the hindpaw involves GFRa+/IB4+ thinly myelinated fibers that express TRPA1 rather than TRPV1 [Akopian et al., 2007; Barabas et al., 2012; Salas et al., 2009]. As in all the in vivo studies mentioned above, the PP1α and eGFP control vectors were injected into the right footpad of male Sprague-Dawley rats and the animals were tested after 7 days for their nocifensive behavior following inoculation of a dilute solution of formalin into the ipsilateral vector-injected footpad. We determined the weighted pain score based on a series of pain responses by the rats [Dubuisson & Dennis, 1977] as in on our prior studies using HSV vectors in the formalin model [Goss et al., 2001]. The data were plotted as the weighted pain score over a period of an hour following formalin injection (FIG. 7) and show the characteristic bi-phasic pain response where the first response represents more acute spontaneous pain while the later response is that seen as a more chronic inflammatory pain response previously shown to involve the TRPA1 receptor. PP1α vector-injected and eGFP control vector-injected animals showed minimal differences in their pain scores in response to formalin injection (FIG. 7), showing that PP1α does not modulate the TRPA1 channel. While not excluding effects on other pain-related channels, this observation is consistent with a certain specificity of PP1α for responses involving TRPV1.

In summary, using the creative cDNA library screening methodology, we have now identified PP1α as a modulator of TRPV1, and shown that it is quite specific for pain behaviors linked to TRPV1 while PP1α has no effect on TRPM8- or TRPA1-involved nocifensive responses. Moreover, we have shown that replication-defective HSV-mediated delivery of PP1α can be used to mitigate pain in a variety of animal models of pain that arise via stimulation of the TRPV1 receptor, suggesting that it may make an effective therapeutic for some types of chronic pain.

EXAMPLE 2

INTRODUCTION AND OBJECTIVES: Increased afferent excitability has been proposed as an important pathophysiological basis of overactive bladder (OAB) and hypersensitive bladder disorders such as interstitial cystitis/bladder pain syndrome (IC/BPS). It has also been reported that transient receptor potential TRPV1 receptors predominantly expressed in C-fiber afferent pathways greatly contribute to afferent sensitization in these disease conditions. As shown in Example 1, HSV vector-mediated PP1α expression leads to the reduction in capsaicin-induced thermal hyperalgesia. Therefore, this led us to investigate the effect of HSV vectors-mediated gene delivery of PP1α on TRPV1-mediated bladder overactivity and pain-related behavior in rats.

METHODS: Replication-deficient HSV vectors encoding PP1α or green fluorescent protein (GFP) as control were injected into the bladder wall of adult female Sprague-Dawley rats. Cystometry (CMG) under urethane anesthesia was performed 1 week after viral injection to evaluate bladder overactivity induced by resiniferatoxin (RTX, a TRPV1 agonist). RTX-induced nociceptive behavior such as licking (lower abdominal licking) and freezing (motionless head-turning) was observed 2 weeks after viral injection. Using immunohistochemistry, GFP expression in L6/S1 DRG and the bladder as well as c-Fos positive cells in the L6 spinal cord dorsal horn were evaluated.

RESULTS: GFP expression was seen in L6/S1 DRG sections. In CMG, the PP1α group showed a significantly ($p<0.05$) smaller reduction (46.5±1.7%) in intercontraction intervals after RTX infusion than the GFP group (65.7±3.8%). The number of RTX-induced freezing behavior, which is correlated with bladder pain sensation, was significantly ($p<0.001$) decreased in PP1α vs. GFP groups. The number of c-Fos positive cells in the L6 spinal dorsal horn was significantly ($p<0.01$) smaller in PP1α vs. GFP rats (24±4 vs. 59±6 cells per section).

CONCLUSIONS: These results indicate that HSV vectors injected into the bladder wall are transported to lumbosacral DRGs that contain bladder afferent neurons, and that PP1α gene delivery in the bladder is effective in suppressing TRPV1-mediated bladder over-activity and pain behavior. Thus, HSV-mediated PP1α gene therapy could be effective for the treatment of OAB and/or hypersensitive bladder disorders such as IC/BPS.

EXAMPLE 3

This Example demonstrates the evaluation of the HSV-PP1a vector in a rat model of Post-Herpetic Neuralgia (PHN) pain.

We had previously established a rat model of Post-Herpetic Neuralgia (PHN) pain (Goins and Kinchington 2011 *J. Neurovirol.* 17(6):590-9; Garry et al., 2005 *Pain* 118(1-2):97-111) by injecting rat footpads with MeWo cells infected with Varicella Zoster Virus (VZV) strain pOka, the parental of the Oka strain which is similar to the vaccine Oka strain (vOka). Since VZV is so cell-associated, one can only inject VZV-infected cells, not purified virus, the way one can do with HSV. Our group and others have seen statistically significant changes in both mechanical (MA) allodynia and thermal hyperalgesia (TH) nocifensive behaviors in rats starting at 1-2 weeks post VZV injection lasting out to 5-9 weeks post VZV, a very robust model of chronic pain that mimics human patient PHN. Other groups have since employed this model to evaluate various drug treatment regimens to determine whether they have any effects on VZV-induced PHN pain, with little to no effect. We have recently tested the HSV-enkephalin vector in this model and have shown that HSV vector-mediated enkephalin expression could block the nocifensive behaviors induced by VZV.

We have since initiated a study in which we compared the HSV vector expressing PP1α in the rat PHN model with vector expressing the GFP reporter gene. Baseline mechanical allodynia (MA) and thermal hyperalgesia (TH) nocifensive responses were measured in ten male Sprague Dawley rats using the von Frey hair up-down method (MA) or the Hargreaves (TH) apparatus. Rats were then injected into their right hindpaws with MeWo infected with $10^5$ pfu VZV strain pOka (parent of Oka, similar to VZV vOka vaccine strain). At 7 and 14 days post VZV, MA and TH behaviors were measured. Next, on Day-0 the rats were injected into the same hindpaws with $10^7$ pfu of either the control GFP-expressing replication-defective HSV vector or the PP1α-expressing vector. At Day-7, rat MA and TH behaviors were assessed. All behavioral scores were plotted as the average response ratio for the ipsilateral injected hindpaw to the contralateral un-injected hindpaw. VZV-PHN mechanical and thermal nocifensive behaviors were observed at Day 0. However, only the control GFP-expressing animals retained these responses at Day 7 while the PP1α-expressing vector dramatically reduced both MA and TH nocifensive behaviors in a statistically significant manner. The average paw withdrawal latency time for the uninjected non-inured rats ranged from 7-10 seconds while those for the VZV-injected/PP1α-vector injected rats ranged from 13-25.

We initially injected VZV pOka into the footpads of 10 Sprague-Dawley rats (Charles River) after measuring baseline MA and TH behaviors. Again, all behaviors are measured for the injected ipsilateral footpad compared to the un-injected contralateral footpad, where if the rat is feeling no pain the ratio will equal 1.0 while if the animal shows nocifensive behaviors the ratio will drop below 1.0 with the greater the drop, the more indicative the magnitude of the painful response. After injection of the VZV-infected MeWo cells into the ipsilateral rat footpads, we again measured MA and TH behaviors and saw that for both MA and TH these responses approached scores around 0.5 or below (FIG. 8), indicative of pain. Next, the first group of 5 rats was injected with $10^7$ pfu of HSV control vector expressing GFP or the HSV-PP1α vector. Again, we measured MA and TH scores weekly following HSV vector injection into the same ipsilateral footpad. As seen in FIG. 8, both the MA and TH scores at day 7 post HSV vector injection reversed the painful responses to values of 1.0 or greater, and in the case of TH behaviors led to scores above 1.0, demonstrating that the HSV-PP1α vector worked to alleviate VZV-induced PHN pain.

We continued to follow the two groups of 5 rats further out, measuring both MA and TH responses weekly following HSV vector injection. Baseline mechanical allodynia (MA) and thermal hyperalgesia (TH) nocifensive responses were measured in ten male Sprague Dawley rats using the von Frey hair up-down method (MA) or the Hargreaves (TH) apparatus. Rats were then injected into their right hindpaws with MeWo cells infected with $10^5$ pfu of VZV strain pOka. At 7 and 14 days post VZV, MA and TH behaviors were again measured. By 14 days post VZV injection, all rats displayed painful behaviors assessed by MA and TH. Having established pain in these rats, on DAY-15 post VZV injection, the rats were injected into the same hindpaws with $10^7$ pfu of either the control GFP-expressing replication-defective HSV vector or the PP1α-expressing rd HSV vector. At weekly intervals shown in the timeline at the bottom of the FIG. 9, rat MA and TH behaviors were assessed. All behavioral scores are plotted as the average response ratio for the ipsilateral injected hindpaw to the contralateral un-injected hindpaw. VZV-PHN mechanical and thermal nocifensive behaviors were observed by 14 days post VZV pOka. However, only the control GFP-expressing animals retained these responses at Day 21 (7 days post HSV vector injection) while the PP1a-expressing vector dramatically reduced both MA and TH nocifensive behaviors in a statistically significant manner. Even at 6 weeks following HSV vector injection, the PP1α vector continues to block the painful behaviors in the PHN rats at statistically significant levels. However, the extent of the response seems to be waning slightly in the thermal pain measurements at 5-6 weeks.

Thus, we have now tested the effects of HSV-PP1α vector mediated expression in a well established model of the chronic pain experienced by VZV infected patients that does not respond well to any standard drug therapies; patients either do not respond at all to drugs, or after short treatment regimens no longer obtain relief from those drugs, reinforcing the unmet need for an effective treatment for PHN pain.

EXAMPLE 4

This Example demonstrates Action of HSV Vector-mediated PP1α in the Complete Freund's Adjuvant (CFA) Pain Model We have previously employed the complete Freund's adjuvant (CFA) model to assess HSV gene therapy modalities such as the glycine receptor (GlyR) (Goss et al., 2011 Mol. Ther. 19(3):500-6) and endomorphin (Hao et al., 2009 Eur. J. Pain 13:38-6). In order to evaluate whether HSV vector mediated expression of PP1α can affect the inflammatory pain seen in rats injected into the footpad with CFA, 200-250 g male Sprague-Dawley rats (N=4/vector group) were injected subcutaneously into the right rear hind-paw with $1\times10^8$ pfu of either a control vector (DAP-GFP), a vector expressing PP1α (DAP-PP1α), or vector expressing Poreless-TRPV1 (DAP-PL). Three weeks later, thermal response was again assessed and the average and standard deviation of the thermal response times (in seconds) shown for the injected right hind-paw as time point 0 days post CFA injection. After this Day 0 measurement, 100 μL of complete Freund's adjuvant (CFA) was injected into the right hind-paw as previously described (Goss et al., 2011) and the thermal response was again assessed at 1, 2 and 3 days post-CFA injection. Thermal pain was assessed 1-4 days post CFA where the inflammatory response is greatest by 24-48 h, but begin to abate and is back to normal or near that by 4-5 days. We noticed that the CFA-injected hind paws were red and inflamed at 24 h, decreased somewhat on day 2, even less so by day 3 and near normal except for some residual scarring on day 4.

Although all the rats displayed TH latency withdrawal times within the range of 6-7 seconds prior to injection of any of the three vectors (DAP-GFP, DAP-PL, and DAP-PP1α), only the rats injected with the DAP-GFP control vector demonstrated a similar latency withdrawal time at 3 weeks post-infection (FIG. S1 Day 0). Rats in the DAP-PL, and DAP-PP1α groups, showed increased withdrawal times between 7.6-8.4 seconds, as we had seen in previous thermal pain analyses demonstrating that the gene products expressed by these vectors alter the thermal pain response. Once the rats were, the DAP-GFP control rat group TH latency withdrawal times dropped from 6 to 2.5 seconds within the first 24 hours after CFA injection. The DAP-PL rats dropped only slightly from 8.4 to 5.9 seconds, while the DAP-GFP group dropped from 7.6 to 7.0 seconds. Even though the DAP-GFP group continued to respond to the thermal source in slightly over 2 seconds at 48 h, the DAP-PL, and DAP-PP1α group thermal times each increased by around 1 second, and basically improved to levels observed at time 0 prior to CFA injection. These results show that like porless-TRPV1, vector-expressed PP1α altered the rats' thermal response during the inflammatory reaction caused by the injection of CFA in a manner similar to which we have previously seen using vectors that express either endomorphin (Hao et al., 2009 Eur. J. Pain 13:38-6) and the glycine receptor (GlyR) (Goss et al., 2011 Mol. Ther. 19(3):500-6). These results support the conclusion that PP1α can ameliorate inflammatory nocifensive behaviors.

All references, including publications, patent applications, and patents, cited herein are hereby incorporated by reference to the same extent as if each reference were individually and specifically indicated to be incorporated by reference and were set forth in its entirety herein. The following references also are expressly incorporated by reference:

Oral presentation at the ASGCT 14th Annual Meeting, May 18-21, 2011 in Seattle, Wash., USA by Dr. Reinhart entitled "An HSV Based Selection Method for Isolation of Negative Regulators of TRPV1".

Oral presentation at the ASGCT 16th Annual Meeting, May 15-18, 2013 in Salt Lake City, Utah, USA by Dr. Glorioso entitled "Identification of a Negative Regulator of TRPV1 Via an HSV Based cDNA Library Screen".

Reinhart et al., "Identification of a Negative Regulator of TRPV1 Via an HSV Based cDNA Library Screen," Abstract [478] for the American Society of Gene & Cell Therapy (ASGCT) 16th Annual Meeting, published Apr. 19, 2013 and associated presentation, given May 18, 2013.

Majima et al., "Herpes Simplex Virus (HSV) Vector-Mediated Gene Delivery of Protein Phosphatase 1α Reduces Bladder Overactivity and Nociception in Rats," Abstract MP1-03, J. Urol., 191(4S) (2014), believed to be available electronically on or about Jan. 4, 2014.

Herpes simplex virus vector-mediated gene delivery of glutamic acid decarboxylase reduces detrusor overactivity in spinal cord injured rats. (2009) Miyazato M, Sugaya K, Goins W F, Goss J R, Chancellor M B, de Groat W C, Glorioso J C, Yoshimura N. Gene Ther. 16(5):660-8. PMCID: PMC2881227.

Suppression of detrusor-sphincter dyssynergia by herpes simplex virus vector-mediated gene delivery of glutamic acid decarboxylase in spinal cord injures rats. (2010) Miyazato M, Sugaya K, Saito S, Chancellor M B, Goins W F, Goss J R, de Groat W C, Glorioso J C, Yoshimura N. J Urol. 184(3):1204-10. PMCID: PMC2921014.

HSV delivery of a ligand-regulated endogenous ion channel gene to sensory neurons results in pain control following channel activation. (2011) Goss J R, Cascio M, Goins W F, Huang S, Krisky D M, Clarke R J, Johnson J W, Yokoyama H, Yoshimura N, Gold M S, Glorioso J C. Mol Ther. 19(3):500-6. PMCID: PMC3048176.

Effects of herpes simplex virus vector-mediated enkephalin gene therapy on bladder overactivity and nociception. (2013) Yokoyama H, Oguchi T, Goins W F, Goss J R, Nishizawa O, de Groat W C, Wolfe D, Krisky D M, Glorioso J C, Yoshimura N. Hum Gene Ther. 24(2):170-80. PMCID: PMC3581021.

Gene therapy for pain: results of a Phase I clinical trial. (2011) Fink D J, Wechuck J, Mata M, Glorioso J C, Goss J, Krisky D, Wolfe D. Ann Neurol. 70(2):207-12. PMCID: PMC3152623.

Gene therapy for bladder overactivity and nociception with herpes simplex virus vectors expressing preproenkephalin. (2009) Yokoyama H, Sasaki K, Franks M E, Goins W F, Goss J R, de Groat W C, Glorioso J C, Chancellor M B, Yoshimura N. Hum Gene Ther. 20(1):63-71. PMCID: PMC2855255.

Protein kinase C epsilon contributes to basal and sensitizing responses of TRPV1 to capsaicin in rat dorsal root ganglion neurons. (2008) Srinivasan R, Wolfe D, Goss J, Watkins S, de Groat W C, Sculptoreanu A, Glorioso J C. Eur J Neurosci. 28(7):1241-54. PMCID: PMC3111963.

HSV-mediated expression of interleukin-4 in dorsal root ganglion neurons reduces neuropathic pain. (2006) Hao S, Mata M, Glorioso J C, Fink D J. Mol Pain. 2:6. PMCID: PMC1395302.

Effects of transgene-mediated endomorphin-2 in inflammatory pain. (2009) Hao S, Wolfe D, Glorioso J C, Mata M, Fink D J. Eur J Pain. 13(4):380-6. PMCID: PMC2656597.

Herpes vector-mediated expression of proenkephalin reduces bone cancer pain. Goss J R, Harley C F, Mata M, O'Malley M E, Goins W F, Hu X, Glorioso J C, Fink D J., Ann Neurol. 2002 52(5):662-5. PMID:12402268.

Antinociceptive effect of a genomic herpes simplex virus-based vector expressing human proenkephalin in rat dorsal root ganglion. (2001) Goss J R, Mata M, Goins W F, Wu H H, Glorioso J C, Fink D J. Gene Ther. 8(7):551-6. PMID: 11319622.

The vanilloid receptor: a molecular gateway to the pain pathway. (2001) Caterina M J, Julius D. Annu Rev Neurosci. 24:487-517. PMID: 11283319.

The capsaicin receptor: a heat-activated ion channel in the pain pathway. (1997) Caterina M J, Schumacher M A, Tominaga M, Rosen T A, Levine J D, Julius D. Nature. 389(6653):816-24. PMID: 9349813.

The cloned capsaicin receptor integrates multiple pain-producing stimuli. (1998) Tominaga M, Caterina M J, Malmberg A B, Rosen T A, Gilbert H, Skinner K, Raumann B E, Basbaum A I, Julius D. Neuron. 21(3):531-43. PMID: 9768840.

Targeting TRP channels for pain relief (2013) Brederson J D, Kym P R, Szallasi A. Eur J Pharmacol. 716(1-3):61-76. PMID: 23500195.

Receptor-targeting mechanisms of pain-causing toxins: How ow? (2012) Bohlen C J, Julius D. Toxicon. 60(3):254-64. PMCID: PMC3383939

Targeting of sodium channel blockers into nociceptors to produce long-duration analgesia: a systematic study and review. (2011) Roberson D P, Binshtok A M, Blasl F, Bean B P, Woolf C J. Br J Pharmacol. 164(1):48-58. PMCID: PMC3171859.

Functionally important amino acid residues in the transient receptor potential vanilloid 1 (TRPV1) ion channel—an overview of the current mutational data. (2013) Winter Z, Buhala A, Ötvös F, Jósvay K, Vizler C, Dombi G, Szakonyi G, Oláh Z. Mol Pain 9:30. PMCID: PMC3707783.

Treatment of trigeminal ganglion neurons in vitro with NGF, GDNF or BDNF: effects on neuronal survival, neurochemical properties and TRPV1-mediated neuropeptide secretion. (2005) Price T J, Louria M D, Candelario-Soto D, Dussor G O, Jeske N A, Patwardhan A M, Diogenes A, Trott A A, Hargreaves K M, Flores C M. BMC Neurosci. 6:4. PMCID: PMC548274.

Activation of CaMKII and ERK1/2 contributes to the time-dependent potentiation of Ca2+ response elicited by repeated application of capsaicin in rat DRG neurons. (2011) Zhang X, Daugherty S L, de Groat W C., Am J Physiol Regul Integr Comp Physiol. 300(3):R644-54. PMCID: PMC3064279.

Activation of NMDA receptors leads to phosphorylation of TRPV1 5800 by protein kinase C and A-Kinase anchoring protein 150 in rat trigeminal ganglia. (2012) Lee J, Chung M-K, Ro J Y. Biochem Biophys Res Commun. 424(2):358-63. PMCID: PMC3408820.

TRPV1 Function in Mouse Colon Sensory Neurons Is Enhanced by Metabotropic 5-Hydroxytryptamine Receptor Activation. (2004) Sugiura T, Bielefeldt K, Gebhart G F. J. Neuroscience, 24(43):9521-30.

Relative roles of protein kinase A and protein kinase C in modulation of transient receptor potential vanilloid type 1 receptor responsiveness in rat sensory neurons in vitro and peripheral nociceptors in vivo. (2006) Varga, A., Bolcskei, K., Szöke, E., Almási, R., Czéh, G., Szolcsányi, J., Petho, G. Neuroscience 140(2):645-57. PMID: 16564637.

$Ca^{++}$/CaMKII switches nociceptor-sensitizing stimuli into desensitizing stimuli. (2012) Hucho T, Suckow V, Joseph E K, Kuhn J, Schmoranzer J, Dina O A, Chen X, Karst M, Bernateck M, Levine J D, Ropers H H., J Neurochem. 123(4):589-601. PMID: 22891703.

AKAP150-mediated TRPV1 sensitization is disrupted by calcium/calmodulin. (2011) Chaudhury S, Bal M, Belugin S, Shapiro M S, Jeske N A. Mol Pain. 7:34. PMCID: PMC3113319.

Cannabinoid WIN 55,212-2 regulates TRPV1 phosphorylation in sensory neurons. (2006) Jeske N A, Patwardhan A M, Gamper N, Price T J, Akopian A N, Hargreaves K M. J Biol Chem. 281(43):32879-90. PMID:16954222.

Regulation of Ca2+-dependent desensitization in the vanilloid receptor TRPV1 by calcineurin and cAMP-dependent protein kinase. (2005) Mohapatra, D. P., Nau, C. J Biol Chem 280(14):13424-32 PMID:15691846.

PP2B/calcineurin-mediated desensitization of TRPV1 does not require AKAP150. (2010) Por E D, Samelson B K, Belugin S, Akopian A N, Scott J D, Jeske N A. Biochem J. 432(3):549-56. PMID:20883208 PMCID:PMC3050517.

An HSV vector system for selection of ligand-gated ion channel modulators. (2007) Srinivasan R, Huang S, Chaudhry S, Sculptoreanu A, Krisky D, Cascio M, Friedman P A, de Groat W C, Wolfe D, Glorioso J C., Nat Methods. 4(9):733-9. PMID:17676048.

A herpes simplex virus vector system for expression of complex cellular cDNA libraries. (2010) Wolfe D, Craft A M, Cohen J B, Glorioso J C. J Virol. 84(14):7360-8. PMID: 20463073.

Inhibition of calcineurin inhibits the desensitization of capsaicin-evoked currents in cultured dorsal root ganglion neurones from adult rats. (1996) Docherty R J, Yeats J C, Bevan S, Boddeke H W. Pflugers Arch. 431(6):828-37. PMID:8927498.

Replication-defective herpes simplex virus vectors for gene transfer in vivo. (1996) Marconi P, Krisky D, Oligino T, Poliani P L, Ramakrishnan R, Goins W F, Fink D J, Glorioso J C. Proc Natl Acad Sci USA. 93(21):11319-20. PMID:8876133.

A new and sensitive method for measuring thermal nociception in cutaneous hyperalgesia. (1988) Hargreaves K, Dubner R, Brown F, Flores C, Joris J. Pain. 32(1):77-88. PMID:3340425.

Downregulation of transient receptor potential melastatin 8 by protein kinase C-mediated dephosphorylation. (2005) Premkumar L S, Raisinghani M, Pingle S C, Long C, Pimentel F. J Neurosci. 25(49):11322-9. PMID:16339027.

Transient receptor potential TRPA1 channel desensitization in sensory neurons is agonist dependent and regulated by TRPV1-directed internalization. (2007) Akopian A N, Ruparel N B, Jeske N A, Hargreaves K M. J Physiol. 583(Pt 1):175-93. PMID:17584831.

TRPA1 is functionally expressed primarily by IB4-binding, non-peptidergic mouse and rat sensory neurons. (2012) Barabas M E, Kossyreva E A, Stucky C L. PLoS One. 2012; 7(10):e47988. PMID:23133534.

TRPA1-mediated responses in trigeminal sensory neurons: interaction between TRPA1 and TRPV1. (2009) Salas M M, Hargreaves K M, Akopian A N. Eur J Neurosci. 29(8):1568-78. PMID:19419422.

The formalin test: a quantitative study of the analgesic effects of morphine, meperidine, and brain stem stimulation in rats and cats. (1977) Dubuisson D, Dennis S G. Pain. 4(2):161-74. PMID:564014.

Varicella zoster virus-induced pain and post-herpetic neuralgia in the human host and in rodent animal models. (2011) Kinchington P R, Goins W F. J Neurovirol. 17(6):590-9. PMID:22205584.

Varicella zoster virus induces neuropathic changes in rat dorsal root ganglia and behavioral reflex sensitisation that is attenuated by gabapentin or sodium channel blocking drugs. (2005) Garry E M, Delaney A, Anderson H A, Sirinathsinghji E C, Clapp R H, Martin W J, Kinchington P R, Krah D L, Abbadie C, Fleetwood-Walker S M. Pain. 118 (1-2):97-111. PMID:16213091

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method comprising administering a pharmaceutical composition comprising a pharmaceutically-acceptable carrier and herpes simplex virus (HSV) vectors comprising an expression cassette, which expression cassette comprises a nucleic acid sequence encoding PP1α operably linked to a promoter, to a mammal in an amount and at a location sufficient to result in HSV vectors within the composition to infect peripheral neurons associated with the sensation of pain, such that the nucleic acid sequences encoding PP1α within said vectors are transcribed within the neurons to produce PP1α within the neurons.

2. The method of claim 1, which mitigates the sensation of pain caused by exposure to capsaicin or Resiniferatoxin (RTx).

3. The method of claim 1, wherein the mammal is human.

4. The method of claim 3, wherein the nucleic acid sequence encoding PP1α encodes the human form of PP1α.

5. The method of claim 3, wherein the promoter is a human promoter.

6. The method of claim 1, wherein the promoter is the hCMV1 promoter.

7. The method of claim 1, wherein the promoter is the ubiquitin (Ub) promoter.

8. The method of claim 1, wherein the promoter is a neuronal-specific promoter.

9. The method of claim 1, wherein the promoter sequence is the transient receptor potential cation channel subfamily V member 1 (TRPV1) promoter.

10. The method of claim 1, wherein the HSV vectors are targeted to specifically infect C-fibers within the mammal.

11. The method of claim 1, wherein the pharmaceutical composition is formulated as a liquid suitable for administration by skin prick, or via subdermal, intramuscular, or parenteral injection.

12. The method of claim 1, wherein the pharmaceutical composition is formulated for transdermal administration.

13. The method of claim 1, wherein the HSV is replication deficient.

14. The method of claim 1, wherein the method is a method of treating pain in a mammal in need thereof, wherein said mammal experiences pain and said administering of the pharmaceutical composition is in an amount and at a location that is sufficient to reduce said pain.

15. The method of claim 14, wherein the mammal is human.

* * * * *